United States Patent
Hersh

(10) Patent No.: US 7,807,396 B2
(45) Date of Patent: Oct. 5, 2010

(54) INSULIN DEGRADING ENZYME ASSAYS FOR TREATMENT OF ALZHEIMER'S DISEASE

(75) Inventor: Louis B. Hersh, Lexington, KY (US)

(73) Assignee: University of Kentucky Research Foundation

(*) Notice: Subject to any disclaimer, the term of this patent is extended or adjusted under 35 U.S.C. 154(b) by 771 days.

(21) Appl. No.: 10/513,470

(22) PCT Filed: Jun. 3, 2003

(86) PCT No.: PCT/US03/17267

§ 371 (c)(1), (2), (4) Date: Aug. 12, 2005

(87) PCT Pub. No.: WO03/102016

PCT Pub. Date: Dec. 11, 2003

(65) Prior Publication Data

US 2006/0087736 A1  Apr. 27, 2006

Related U.S. Application Data

(62) Division of application No. 09/792,079, filed on Feb. 26, 2001, now abandoned.

(60) Provisional application No. 60/184,826, filed on Feb. 24, 2000.

(51) Int. Cl.
*G01N 33/573* (2006.01)

(52) U.S. Cl. .................................... 435/7.72

(58) Field of Classification Search .................. None
See application file for complete search history.

(56) References Cited

U.S. PATENT DOCUMENTS

| | | | |
|---|---|---|---|
| 4,897,389 A | 1/1990 | Aroonsakul | |
| 5,554,601 A | 9/1996 | Simpkins et al. | |
| 5,624,894 A | 4/1997 | Bodor | |
| 5,952,346 A | 9/1999 | Heitsch et al. | |
| 6,333,317 B1 | 12/2001 | Lee et al. | |
| 2002/0091072 A1 | 7/2002 | Eckman et al. | |
| 2004/0038302 A1 | 2/2004 | Nitsch et al. | |

FOREIGN PATENT DOCUMENTS

| | | |
|---|---|---|
| WO | WO 02/25279 | 9/2001 |
| WO | WO 02/22794 | 3/2002 |
| WO | WO 02/087552 | 11/2002 |

OTHER PUBLICATIONS

Blaustein. Minireview: Neuronal steroid hormone receptors: they're not just for hormones anymore. Endocrinology. Mar. 2004;145(3):1075-81. Epub Dec. 11, 2003.*
Carson JA, Turner AJ. J Neurochem. Apr. 2002;81(1):1-8. *Beta-amyloid catabolism: roles for neprilysin (NEP) and other metallopeptidases?*
Chesneau V, Vekrellis K, Rosner MR, Selkoe DJ. Biochem J. Oct. 15, 2000;351 Pt 2:509-16. *Purified recombinant insulin-degrading enzyme degrades amyloid beta-protein but does not promote its oligomerization.*
Eckman EA, Watson M, Marlow L, Sambamurti K, Eckman CB. J Biol Chem. Jan. 24, 2003;278(4):2081-4. Epub Dec. 2, 2002. *Alzheimer's disease beta-amyloid peptide is increased in mice deficient in endothelin-converting enzyme.*
Hama E, Shirotani K, Masumoto H, Sekine-Aizawa Y, Aizawa H, Saido TC. J Biochem (Tokyo). Dec. 2001;130(6):721-6. *Clearance of extracellular and cell-associated amyloid beta peptide through viral expression of neprilysin in primary neurons.*
Haouas H, Morello D, Lavenu A, Billard M, Jasmin C, Boucheix C. Biochem Biophys Res Commun. Feb. 27, 1995;207(3):933-42. *Characterization of the 5' region of the CD10/neutral endopeptidase 24.11 gene.*
Henderson VW, Paganini-Hill A, Miller BL, Elble RJ, Reyes PF, Shoupe D, McCleary CA, Klein RA, Hake AM, Farlow MR. Neurology. Jan. 25, 2000;54(2):295-301. *Estrogen for Alzheimer's disease in women: randomized, double-blind, placebo-controlled trial.*
Howell S, Nalbantoglu J, Crine P. Peptides. 1995;16(4):647-52. *Neutral endopeptidase can hydrolyze beta-amyloid(1-40) but shows no effect on beta-amyloid precursor protein metabolism.*
Ishimaru F, Mari B, Shipp MA. Blood. Jun. 1, 1997;89(11):4136-45. *The type 2 CD10/neutral endopeptidase 24.11 promoter: functional characterization and tissue-specific regulation by CBF/NF-Y isoforms.*
Iwata N, Tsubuki S, Takaki Y, Watanabe K, Sekiguchi M, Hosoki E, Kawashima-Morishima M, Lee HJ, Hama E, Sekine-Aizawa Y, Saido TC. Nat Med. Feb. 2000;6(2):143-50. *Identification of the major Abeta1-42-degrading catabolic pathway in brain parenchyma: suppression leads to biochemical and pathological deposition.*
Iwata N, Tsubuki S, Takaki Y, Shirotani K, Lu B, Gerard NP, Gerard C, Hama E, Lee HJ, Saido TC. Science. May 25, 2001;292(5521):1550-2. *Metabolic regulation of brain Abeta by neprilysin.*
Kurochkin IV, Goto S. FEBS Lett. May 23, 1994;345(1):33-7. *Alzheimer's beta-amyloid peptide specifically interacts with and is degraded by insulin degrading enzyme.*
Kurochkin IV. Trends Biochem Sci. Jul. 2001;26(7):421-5. *Insulin-degrading enzyme: embarking on amyloid destruction.*
Li C, Hersh LB. Arch Biochem Biophys. Oct. 1, 1998;358(1):189-95. *Characterization of the promoter region of the rat neprilysin gene.*
Li C, Booze RM, Hersh LB. J Biol Chem. Mar. 17, 1995;270(11):5723-8. *Tissue-specific expression of rat neutral endopeptidase (neprilysin) mRNAs.*
Li C, Guojin Chen, Norma P. Gerard, Craig Gerard, Carmen R Bozic, Louis B. Hersh "Comparison of the structure and expression of the human rat neprilysin (endopeptidase 24.11)- encoding genes." Gene. 164 (1995) pp. 363-366.

(Continued)

Primary Examiner—Daniel E Kolker
Assistant Examiner—Gregory S Emch
(74) Attorney, Agent, or Firm—McDermott Will & Emery LLP

(57) ABSTRACT

Estrogen has been shown to increase the expression and activity of amyloid peptide inactivating enzymes in the brain. Peptides have been shown to increase the activity of an amyloid peptide inactivating enzyme. Methods of identifying compounds for, and methods of treating patients with, Alzheimer's Disease is disclosed.

7 Claims, 19 Drawing Sheets

OTHER PUBLICATIONS

Marr RA, Rockenstein E, Mukherjee A, Kindy MS, Hersh LB, Gage FH, Verma IM, Masliah E. J Neurosci. Mar. 15, 2003;23(6):1992-6. *Neprilysin gene transfer reduces human amyloid pathology in transgenic mice.*
McDermott JR, Gibson AM. Neurochem Res. Jan. 1997;22(1):49-56. *Degradation of Alzheimer's beta-amyloid protein by human and rat brain peptidases: involvement of insulin-degrading enzyme.*
Miller BC, Eckman EA, Sambamurti K, Dobbs N, Chow KM, Eckman CB, Hersh LB, Thiele DL. Proc Natl Acad Sci U S A. May 13, 2003;100(10):6221-6. Epub May 5, 2003. *Amyloid-beta peptide levels in brain are inversely correlated with insulysin activity levels* in vivo.
Mohajeri MH, Wollmer MA, Nitsch RM. J Biol Chem. Sep. 20, 2002;277(38):35460-5. Epub Jul. 8, 2002. *Abeta 42-induced increase in neprilysin is associated with prevention of amyloid plaque formation* in vivo.
Perez A, Morelli L, Cresto JC, Castano EM. Neurochem Res. Feb. 2000;25(2):247-55. *Degradation of soluble amyloid beta-peptides 1-40, 1-42, and the Dutch variant 1-40Q by insulin degrading enzyme from Alzheimer disease and control brains.*
Petanceska SS, Nagy V, Frail D, Gandy S. Exp Gerontol. Dec. 2000;35(9-10):1317-25. *Ovariectomy and 17beta-estradiol modulate the levels of Alzheimer's amyloid beta peptides in brain.*
Pinto FM, Armesto CP, Magraner J, Trujillo M, Martin JD, Candenas ML. Endocrinology. Jun. 1999;140(6):2526-32. *Tachykinin receptor and neutral endopeptidase gene expression in the rat uterus: characterization and regulation in response to ovarian steroid treatment.*
Qiu WQ, Walsh DM, Ye Z, Vekrellis K, Zhang J, Podlisny MB, Rosner MR, Safavi A, Hersh LB, Selkoe DJ. J Biol Chem. Dec. 4, 1998;273(49):32730-8. *Insulin-degrading enzyme regulates extracellular levels of amyloid beta-protein by degradation.*
Shen R, Sumitomo M, Dai J, Hardy DO, Navarro D, Usmani B, Papandreou CN, Hersh LB, Shipp MA, Freedman LP, Nanus DM. Mol Cell Endocrinol. Dec. 22, 2000;170(1-2):131-42. Identification and characterization of two androgen response regions in the human neutral endopeptidase gene.
Shirotani K, Tsubuki S, Iwata N, Takaki Y, Harigaya W, Maruyama K, Kiryu-Seo S, Kiyama H, Iwata H, Tomita T, Iwatsubo T, Saido TC. J Biol Chem. Jun. 15, 2001;276(24):21895-901. Epub Mar. 6, 2001. Neprilysin degrades both amyloid beta peptides 1-40 and 1-42 most rapidly and efficiently among thiorphan- and phosphoramidon-sensitive endopeptidases.
Song ES, Mukherjee A, Juliano MA, Pyrek JS, Goodman JP Jr, Juliano L, Hersh LB. J Biol Chem. Jan. 12, 2001;276(2):1152-5. Analysis of the subsite specificity of rat insulysin using fluorogenic peptide substrates.
Tharaux PL, Stefanski A, Ledoux S, Soleilhac JM, Ardaillou R, Dussaule JC.Am J Physiol. Jun. 1997;272(6 Pt 1):C1836-43. *EGF and TGF-beta regulate neutral endopeptidase expression in renal vascular smooth muscle cells.*
Vekrellis K, Ye Z, Qiu WQ, Walsh D, Hartley D, Chesneau V, Rosner MR, Selkoe DJ. J Neurosci. Mar. 1, 2000;20(5):1657-65. Neurons regulate extracellular levels of amyloid beta-protein via proteolysis by insulin-degrading enzyme.
Abraham R, Myers A, Wavrant-Devrieze F, Hamshere ML, Thomas HV, Marshall H, Compton D, Spurlock G, Turic D, Hoogendoorn B, Kwon JM, Petersen RC, Tangalos E, Norton J, Morris JC, Bullock R, Liolitsa D, Lovestone S, Hardy J, Goate A, O'Donovan M, Williams J, Owen MJ, Jones L. "Substantial Linkage Disequilibrium Across the Insulin-Degrading Enzyme Locus But No Association With Late-Onset Alzheimer's Disease" Hum Genet. Dec. 2001; 109(6):646-52.
Selkoe DJ "Clearing the Brain's Amyloid Cobwebs" Neuron. Oct. 25, 2001;32(2):177-80.
Fricke B, Betz R, Friebe S, "A Periplasmic Insulin-Cleaving Proteinase (ICP) From Acinetobacter Calcoaceticus Sharing Properties With Protease II From *Escherichia coli* and IDE From Eukaryotes" Chemical Abstracts, 1995;123:77933X.
Espinosa R III, Lemons RS, Perlman RK, Kuo WL, Rosner MR, Lebeau MM "Localization of the Gene Encoding Insulin-Degrading Enzyme to Human Chromosome 10, Bands Q23-Q25" J-Biochem Genetics, 1992; 116:77617C.
Sakamoto T, "Establishment of Radioimmunoassay for Human Crythrocyte Insulin-Degrading Enzyme (IDE) and Its Clinical Application" 7-Enzymes, 1989; 111:92605N.
Sodeyama N, Mizusawa H, Yamada M, Itoh Y, Otomo E, Matsushita M, "Lack of Association of Neprilysin Polymorphism With Alzheimer's Disease and Alzheimer's Disease-Type Neuropathological Changes" J. Neurol Neurosurg Psychiatry 2001; 71:817-824.
Nitsch et al. "Upregulation of Neprilysin Prevents Amyloid Plaque in SWAPP Transgenic Mice", Soc. for Neuroscience Abstracts., vol. 27, No. 1, pp. 926, Aug. 17, 2001.
Tanzi et al. "Clearance of Alzheimer's AB Peptide: The Many Roads to Perdition", Neuron Sep. 2004, vol. 43. No. 5, pp. 605-608.
Koji Yasojima, Haruhiko Akiyama, Edith G. McGeer, and Patrick L. McGeer, "Reduced Neprilysin in High Plaque Areas of Alzheimer Brains; A Possible Relationship to Deficient Degradation of β-Amyloid Peptide", Neuroscience Letters 297, (2001) pp. 97-100.
Atish Mukherjee, Eun-Suk Song, Muthoni Kihiko-Ehmann, Jack P. Goodman Jr, Jan St. Pyrek, Steven Estus, and Louis B. Hersh, "Insulysin Hydrolyzes Amyloid β Peptides to Products That Are Neither Neurotoxic Nor Deposit on Amyloid Plaques", The Journal of Neuroscience, Dec. 1, 2000, 20(23) pp. 8745-8749.
Yoshie Takaki, Nobuhisa Iwata, Satoshi Tsubuki, Sayuri Taniguchi, Satoshi Toyoshima, Bao Lu, Norma P. Gerard, Craig Gerard, Hahn-Jun Lee, Keiro Shirotani, and Takaomi C. Saido, "Biochemical Identification of the Neutral Endopeptidase Family Member Responsible for the Catabolism of Amyloid β Peptide in the Brain," The Japanese Biochemical Society vol. 128, (2000) pp. 897-902.
Igor V. Kurochkin, Sataro Goto, "Alzheimer's β-Amyloid Peptide Specifically Interacts With and is Degraded by Insulin Degrading Enzyme", FEBS Letters 345 (1994) 33-37.
Fukami S, Watanabe K, Iwata N, Haraoka J, Lu B, Gerard NP, Gerard C, Fraser P, Westaway D, St. George-Hyslop P, Saido TC. "a β-Degrading Endopeptidase, Neprilysin, in Mouse Brain; Synaptic and Axonal Localization Inversely Correlating With a β-Pathology." Neurosci Res. May 2002; 43(1):39-56.
Hauss-Wegrzyniak B, Wenk GL. "β-Amyloid Deposition in the Brains of Rats Chronically Infused With Thiorphan or Lipopolysaccharide: The Role of Ascorbic Acid in the Vehicle" Neurosci Lett. Apr. 5, 2002;322(2):75-8.
Oda M, Morino H, Maruyama H, Terasawa H, Izumi Y, Torii T, Sasaki K, Nakamura S, Kawakami H. "Dinucleotide Repeat Polymorphins in the Neprilysin Gene Are Not Associated With Sporadic Alzheimer's Disease." Neurosci Lett. Mar. 1, 2002;320(12):105-7.
Clark, et al., 1993, Arch. Neurol., 50, pp. 1164-1172.

* cited by examiner

Lane 1: control, $^{125}$I-Aβ1-40 deposited alone; 2: no plaque; 3: heat inactivated IDE; 4: 500ng IDE; 5: 50ng IDE; 6: 5ng IDE; 7 0.5 ng IDE

Positions of cleavage in Aβ$_{1-40}$

Asp-Ala-Glu-Phe-Arg-His-Asp-Ser-Gly-Tyr-Glu-Val-His$^{13}$↓His$^{14}$↓Gln$^{15}$-Lys-Leu-Val$^{18}$↓Phe$^{19}$↓Phe$^{20}$↓Ala$^{21}$-Glu-Asp-Val-Gly-Ser-Asn-Lys$^{28}$↓Gly$^{29}$-Ala-Ile-Gly-Leu-Met-Val-Gly-Gly-Val-Val

Positions of cleavage in Aβ$_{1-42}$

Asp-Ala-Glu-Phe-Arg-His-Asp-Ser-Gly-Tyr-Glu-Val-His$^{13}$↓His$^{14}$↓Gln$^{15}$-Lys-Leu-Val-Phe$^{19}$↓Phe$^{20}$↓Ala$^{21}$-Glu-Asp-Val-Gly-Ser-Asn-Lys-Gly-Ala-Ile-Gly-Leu-Met-Val-Gly-Gly-Val-Val-Ile-Ala

FIGURE 6

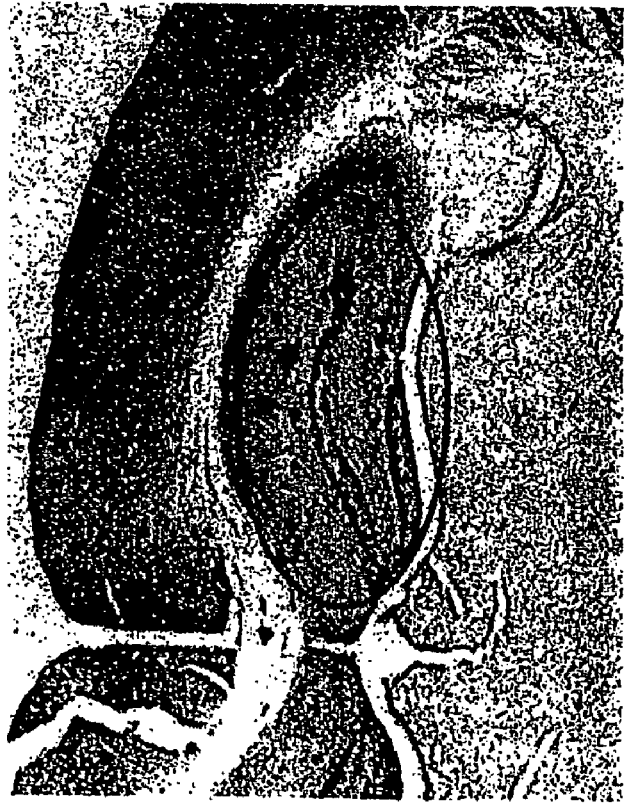
APP+/- X NEP Virus    B
APP+/- X Control Virus    A
FIGURE 12

Effect of ovariectomy and estrogen replacement on NEP activity in rat brain

| | Number | NEP Activity in hippocampus (pmol/ug protein). mean±SEM | NEP Activity in cerebellum (pmol/ug protein). mean±SEM | NEP Activity in caudate (pmol/ug protein). mean±SEM |
|---|---|---|---|---|
| Control with ovary | 6 | 85±10 | 122±18 | 246±80 |
| ovx | 6 | 76±15 | 102±17 | 233±20 |
| ovx+estrogen | 6 | 101±16 | 135±14 | 254±37 |

FIGURE 15

Peptides increase insulin degrading enzyme activity. A lead to new pharmacological agents.

| Peptide | Increase in insulin degrading enzyme activity. |
|---|---|
| beta endorphin | 2 |
| Dynorphin A-13 | 3.5 |
| Dynorphin B9 | 5 |
| Dynorphin A-17 | 5 |
| Bradykinin | 6 |

FIGURE 17

SEQUENCE LISTING

```
<160> NUMBER OF SEQ ID NOS: 14

<210> SEQ ID NO 1
<211> LENGTH: 14
<212> TYPE: PRT
<213> ORGANISM: Homo sapiens

<400> SEQUENCE: 1

Asp Ala Glu Phe Arg His Asp Ser Gly Tyr Glu Val His His
1               5                   10

<210> SEQ ID NO 2
<211> LENGTH: 13
<212> TYPE: PRT
<213> ORGANISM: Homo sapiens

<400> SEQUENCE: 2

Asp Ala Glu Phe Arg His Asp Ser Gly Tyr Glu Val His
1               5                   10

<210> SEQ ID NO 3
<211> LENGTH: 18
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val

<210> SEQ ID NO 4
<211> LENGTH: 19
<212> TYPE: PRT
<213> ORGANISM: Homo sapiens
```

-continued

```
<400> SEQUENCE: 4

Asp Ala Glu Phe Arg His Asp Ser Gly Tyr Glu Val His His Gln Lys
1               5                   10                  15

Leu Val Phe

<210> SEQ ID NO 5
<211> LENGTH: 28
<212> TYPE: PRT
<213> ORGANISM: Homo sapiens

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys
            20                  25

<210> SEQ ID NO 6
<211> LENGTH: 20
<212> TYPE: PRT
<213> ORGANISM: Homo sapiens

<400> SEQUENCE: 6

Asp Ala Glu Phe Arg His Asp Ser Gly Tyr Glu Val His His Gln Lys
1               5                   10                  15

Leu Val Phe Phe
            20

<210> SEQ ID NO 7
<211> LENGTH: 21
<212> TYPE: PRT
<213> ORGANISM: Homo sapiens

<400> SEQUENCE: 7

Phe Ala Glu Asp Val Gly Ser Asn Lys Gly Ala Ile Ile Gly Leu Met
1               5                   10                  15

Val Gly Gly Val Val
            20

<210> SEQ ID NO 8
<211> LENGTH: 12
<212> TYPE: PRT
<213> ORGANISM: Homo sapiens

<400> SEQUENCE: 8

Gly Ala Ile Ile Gly Leu Met Val Gly Gly Val Val
1               5                   10

<210> SEQ ID NO 9
<211> LENGTH: 20
<212> TYPE: PRT
<213> ORGANISM: Homo sapiens

<400> SEQUENCE: 9

Ala Glu Asp Val Gly Ser Asn Lys Gly Ala Ile Ile Gly Leu Met Val
1               5                   10                  15

Gly Gly Val Val
            20

<210> SEQ ID NO 10
<211> LENGTH: 22
<212> TYPE: PRT
<213> ORGANISM: Homo sapiens
```

```
<400> SEQUENCE: 10

Phe Phe Ala Glu Asp Val Gly Ser Asn Lys Gly Ala Ile Ile Gly Leu
1               5                   10                  15

Met Val Gly Gly Val Val
            20

<210> SEQ ID NO 11
<211> LENGTH: 26
<212> TYPE: PRT
<213> ORGANISM: Homo sapiens

<400> SEQUENCE: 11

Gln Lys Leu Val Phe Phe Ala Glu Asp Val Gly Ser Asn Lys Gly Ala
1               5                   10                  15

Ile Ile Gly Leu Met Val Gly Gly Val Val
            20                  25

<210> SEQ ID NO 12
<211> LENGTH: 40
<212> TYPE: PRT
<213> ORGANISM: Homo sapiens

<400> SEQUENCE: 12

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 13
<211> LENGTH: 42
<212> TYPE: PRT
<213> ORGANISM: Homo sapiens

<400> SEQUENCE: 13

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 14
<211> LENGTH: 9
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: A 2-Aminobenzoic acid (Abz) group is attached
      to the end terminus.
<220> FEATURE:
<221> NAME/KEY: MISC_FEATURE
<222> LOCATION: (9)..(9)
<223> OTHER INFORMATION: ethylene diamine 2, 4-dinitrophenyl is
      attached to the C terminal.

<400> SEQUENCE: 14

Gly Gly Phe Leu Arg Lys His Gly Gln
1               5
```

INSULIN DEGRADING ENZYME ASSAYS FOR TREATMENT OF ALZHEIMER'S DISEASE

RELATED APPLICATIONS

This application claims priority to PCT/US03/17267, filed Jun. 3, 2003 and application Ser. No. 10/159,279, filed Jun. 3, 2003, which is a continuation-in-part application of application Ser. No. 09/792,079, filed Feb. 26, 2001, abandoned, which claims priority to application Ser. No. 60/184,826, filed Feb. 24, 2000.

This invention is a divisional continuation-in-part of U.S. patent application Ser. No. 09/792,079 filed on Feb. 26, 2001 now abandoned, which claims priority to U.S. Provisional Patent Application No. 60/184,826 filed on Feb. 24, 2000, now expired.

GOVERNMENT INTEREST IN THE INVENTION

This invention was made with Government support under Grant No. DA 02243 and DA 07062 awarded by the National Institute on Drug Abuse, and Grant No. AG 05893 awarded by the National Institute on Aging. The Government has certain rights in this invention.

BACKGROUND OF THE INVENTION

1. Field of the Invention

The present invention relates to a method of preventing amyloid plaque formation and/or growth by reacting amyloid peptides with an enzyme that recognizes amyloid peptides, and inactivates them. The present invention also relates to a method of treating Alzheimer's disease by either administering an amyloid peptide degrading enzyme while minimizing or eliminating toxic side effects associated with amyloid peptide byproducts or by increasing the synthesis of the enzyme by administration of pharmacological agents that regulate the expression of the amyloid peptide degrading enzyme or by increasing the activity of the enzyme by administration of pharamacological agents.

2. Brief Description of the Related Art

Considerable effort has been expended in identifying the beta and gamma secretases that process the amyloid precursor protein to form the Aβ peptides. The goal of such studies has been to develop specific inhibitors of these enzymes in the hope that such compounds would inhibit the formation of amyloid plaques. The recent report of an aspartyl protease, which appears to be a true beta secretase (R. Vassar et al. (1999) *Science* 286, 735-741), provides optimism that this approach can soon be tested.

An alternative strategy is to hydrolyze Aβ peptides before they form amyloid plaques or at least prevent the further development of existing plaques. It may also be possible to remove existing plaques by hydrolyzing any plaque derived Aβ peptide in equilibrium with free Aβ peptide. We test this approach using the zinc metallopeptidases insulysin (also referred to as insulin degrading enzyme, IDE, EC. 3.4.22.11) and neprilysin (also known to as endopeptidase 24.11, NEP, CALLA), although other peptidases such as endopeptidase 24.15, endopeptidase 24.16, endothelin converting enzyme and angiotensin converting enzyme can be employed. There are a number of reasons to using insulysin and neprilysin for this purpose. First, as noted below, both insulysin and neprilysin cleave $A\beta_{1-40}$ and $A\beta_{1-42}$ into what appears to be innocuous products. Second, both insulysin and neprilysin are a true peptidase in that they do not hydrolyze proteins. The enzymes cleave a limited number of peptides in vitro including insulin and insulin related peptides, β endorphin, enkephalins, substance P and Aβpeptides. Third, cell surface forms of insulysin and neprilysin have been described as well as a secreted form of insulysin. Lastly, insulysin and neprilysin have been suggested to be physiological Aβ metabolizing enzymes.

Kurichkin and Goto (I. V. Kurochkin and S. Gato (1994) *FEBS Lett.* 345, 33-37) first reported that insulysin enzyme can hydrolyze $A\beta_{1-40}$. This finding was confirmed in two separate studies (W. Q. Qul et al. (1998) *J. Biol. Chem.* 273, 32730-32738; and J. R. McDermott and A. M. Gibson (1997) *Neurochem. Res.* 22, 49-56); one of these (W. Q. Qui et al. (1998) *J. Biol. Chem.* 273, 32730-32738) was a collaboration with the applicant/inventor. Selkoe has proposed that insulysin could play a role in determining Aβ peptide levels after their secretion from neuronal and microglial cells (K. Vekrellis et al. (1999) *Soc. For Neurosci Abstracts* 25, 302). It was suggested that factors that reduce insulysin activity, i.e. oxidative damage, can lead to decreased Aβ metabolism and increased amyloid deposits (I V. Kurochkin and S. Gato (1994) *FEBS Lett.* 345, 33-37). Although these studies demonstrated that insulysin can hydrolyze $A\beta_{1-40}$, they involved the use of either partially purified enzyme preparations such that the products of the reaction could have arisen from secondary cleavages by contaminating peptidases (I. V. Kurochkin and S. Gato (1994) *FEBS Lett.* 345, 33-37; and J. R. McDermott and A. M. Gibson (1997) *Neurochem. Res.* 22, 49-56), or the reaction products were not identified (I. V. Kurochkin and S. Gato (1994) *FEBS Lett.* 345, 33-37). Furthermore, it was not determined whether the products of insulysin action on $A\beta_{1-40}$ are neurotoxic or could contribute to amyloid plaque formation, and $A\beta_{1-42}$ was not tested as a substrate.

Howell et al (S. Howell, J. Nalbantogluand and P. Crine, *Peptides* (1995), 16 647-652) first showed that neprilysin could hydrolyze $A\beta_{1-40}$.

Thus, there is a need in the art for a method of preventing amyloid plaque deposition and methods for treating Alzheimer's disease while minimizing toxic side effects.

Sequence listing ASCII text-file "10_413,470 Sequence Listing filing.txt" created on Mar. 5, 2010, 4 KB in size is incorporated by reference.

SUMMARY OF THE INVENTION

The present invention has met the hereinbefore-described need.

It is an object of this invention to provide a method for preventing formation or growth of amyloid fibrils or plaques without causing neurotoxicity, comprising administering an inactivating effective amount of an amyloid peptide inactivating enzyme to a mammal in need thereof. The enzyme may be a peptidase. The enzyme may be insulysin (also known as insulin degrading enzyme or IDE), neprilysin (also known to as endopeptidase 24.11, NEP, CALLA) or endopeptidase 24.15, endopeptidase 24.16, endothelin converting enzyme, angiotensin converting enzyme or similar peptidases.

It is also an object of the invention to provide a method for preventing formation or growth of amyloid plaque without causing neurotoxicity, comprising:
 a) generating a recombinant viral or plasmid vector comprising a DNA sequence encoding an amyloid peptide inactivating enzyme operatively linked to a promoter;
 b) transfecting in vitro a population of cultured neural cells or fibroblasts with said recombinant vector, resulting in a population of transfected neural cells or fibroblasts and c) transplanting said transfected neural cells or fibroblasts by injection to the brain of a mammalian host, such that expression of said DNA sequence within said brain results in inactivation of said amyloid peptides.

Another object of the invention is to provide a method for preventing formation or growth of amyloid plaque without causing neurotoxicity, comprising:
 a) generating a recombinant viral or plasmid vector comprising a DNA sequence encoding an amyloid peptide inactivating enzyme operatively linked to a promoter; and
 b) injecting said vector to the brain of a mammalian host, such that expression of said DNA sequence within said brain results in inactivation of said amyloid peptides.

Another object of the invention is to provide a method for preventing formation or growth of amyloid plaque without causing neurotoxicity, comprising:
 a) generating and purifying recombinant amyloid peptide inactivating enzyme and
 b) injecting said amyloid peptide inactivating enzyme to the brain via a pump delivery system.

It is another object of the invention to use pharmacological agents to induce the synthesis of endogenous amyloid inactivating enzymes such as insulysin or neprilysin within the brain of affected individuals.

It is a further object of the invention to provide steroids and analogs thereof to induce the synthesis of an endogenous amyloid inactivating enzymes such as insulysin or neprilysin within the affected individuals.

Another object of the invention is to provide a method for treating a patient with Alzheimer's Disease comprising administering a pharmaceutically effective amount of a steroid or analog thereof to induce the synthesis of an endogenous amyloid inactivating enzymes such as neprilysin within the affected individuals.

Another object of the invention is to use pharmacological agents to increase the activity of amyloid inactivating enzymes such as insulysin or neprilysin within the brain of affected individuals.

It is a further object of the invention to administer a pharmacologically effective amount of a peptide derivative or analog thereof or a combination of such agents including dynorphin, endorphin and bradykinin analogs to increase the activity of an endogenous amyloid inactivating enzyme such as insulysin or neprilysin within Alzheimer's patients.

It is still a further object of the invention to use pharmacological agents to modulate the activity of hormones to thereby increase the activity of an endogenous amyloid inactivating enzyme such as insulysin or neprilysin within Alzheimer's patients.

These and other objects of the invention will be more fully understood from the following description of the invention, the referenced drawings attached hereto and the claims appended hereto.

BRIEF DESCRIPTION OF THE DRAWINGS

FIG. 6 shows positions of cleavage by insulysin within the $A\beta_{1-40}$ (SEQ ID NO: 12) and $A\beta_{1-42}$ (SEQ ID NO: 13) sequences. The primary cleavage sites are noted with the thick arrows.

FIG. 7A shows the effect of incubation with insulysin on the neurotoxic effects of $A\beta_{1-40}$. FIG. 7B shows the effect of incubation with insulysin on the neurotoxic effects of $A\beta_{1-42}$. * designates p=<0.01 relative to the Aβ treated sample as determined by ANOVA.

FIG. 9A shows the effect of incubation with insulysin on the deposition of $A\beta_{1-40}$. $A\beta_{1-40}$ (0.1 nM) was mixed with the indicated amount of purified insulysin and then added to synthaloid in 96 well plates. Deposition was permitted to occur over a 4 hr time period. FIG. 9B shows the effect of preincubation with insulysin on the deposition of $A\beta_{1-40}$. $A\beta_{1-40}$ (1 nM) was preincubated for 60 minutes the indicated amount of purified insulysin. The incubation mixtures were then added to synthaloid in 96 well plates and deposition was permitted to occur over a 4 hr time period. * indicates P=<0.01 as determined by ANOVA.

FIGS. 12 A and 12 B respectively show a brain section showing the hippocampus of a 9 month transgenic mouse that expresses human amyloid precursor protein (FIG. 12A) the hippocampus of a same aged mouse that received by injection a viral construct that produces neprilysin (FIG. 12B).

FIG. 15 shows the effect of ovariectomy and estrogen replacement on neprilysin activity in rat brain.

FIG. 17 shows the effect other peptides on increasing the activity of purified insulin degrading activity.

DETAILED DESCRIPTION OF THE INVENTION

Figure 1:
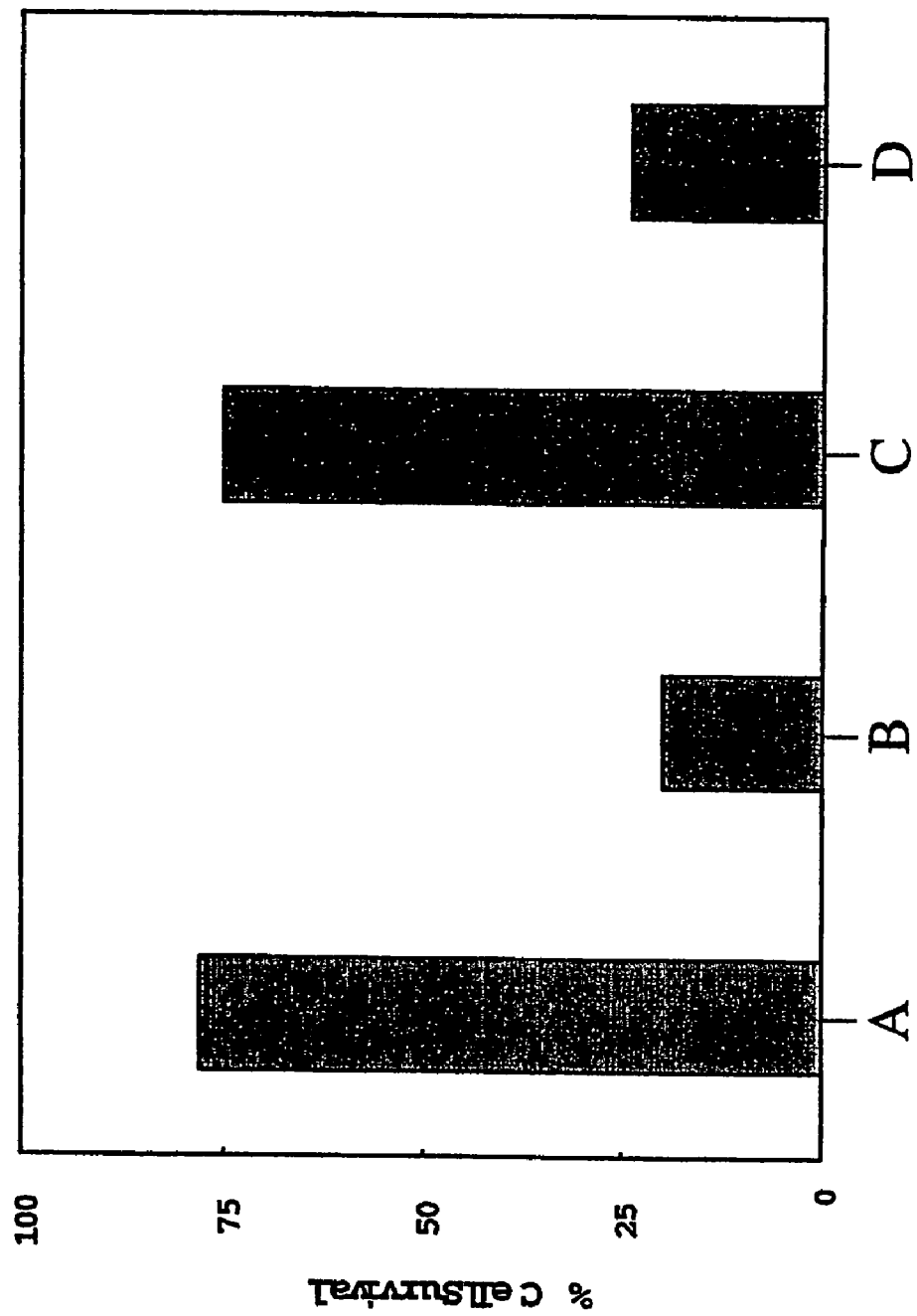
FIG. 1 shows percent survival of hippocampal cells incubated in media containing $A\beta_{1-42}$ with or without insulysin.
Figure 2:
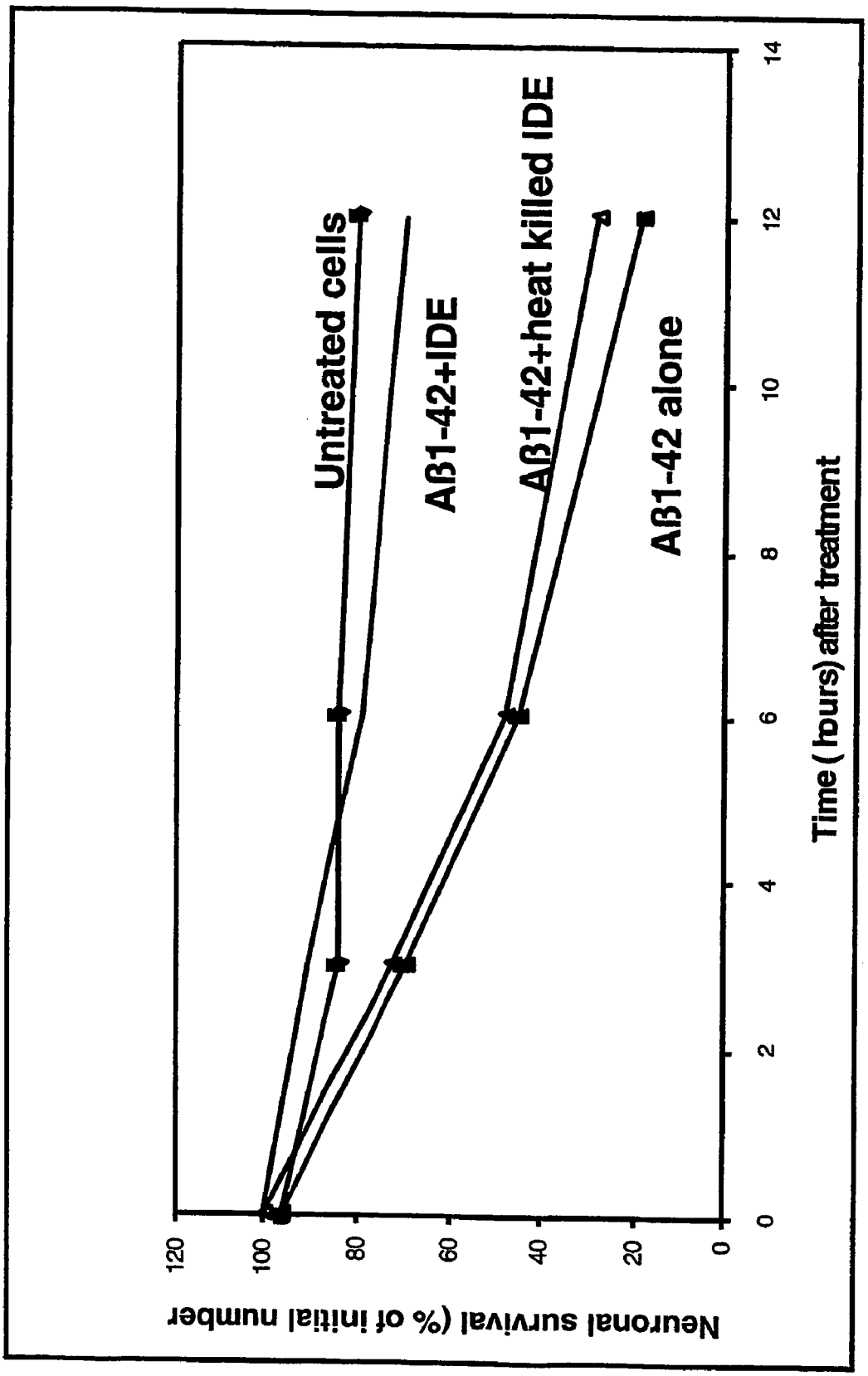
FIG. 2 shows that hippocampal cells treated with insulysin are protected against $A\beta_{1-42}$ induced neurotoxic injury.
Figure 3:
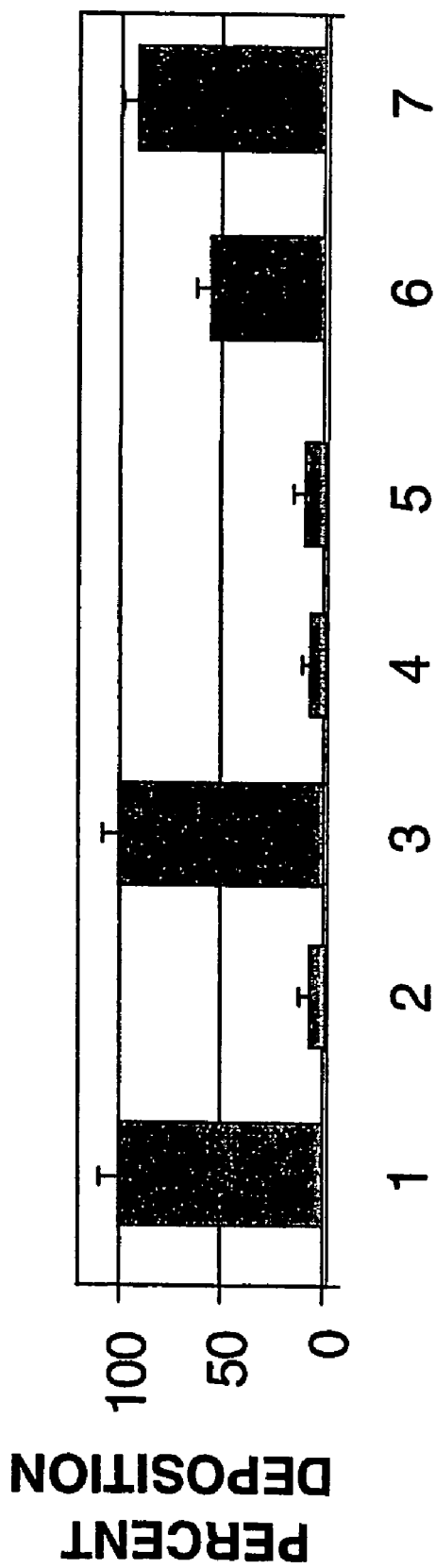
FIG. 3 shows that insulysin prevents $A\beta_{1-40}$ deposition onto plaques.

As used herein, the term "patient" includes members of the animal kingdom including but not limited to human beings.

As used herein, the term "mammalian host" includes members of the animal kingdom including but not limited to human beings.

As used herein, the term "brain tissue" refers to tissue that comprises neural tissue, including hippocampal and cortical tissue.

As used herein, "amyloid peptide inactivating enzyme" encompasses a group of functionally or structurally related proteins that bind to amyloid peptides, and prevent the peptides from depositing as plaques or fibrils. Preferably, toxic side-effects is minimized. By "inactivating" it is meant that the enzyme may functionally prevent amyloid peptides from forming plaques. Preferably, "inactivating" refers to degradation of the amyloid peptide. More preferably, the enzyme is a peptidase. Most preferably, the enzyme is insulysin (insulin degrading enzyme) or neprilysin (endopeptidase 24.11), although other possibilities include endopeptidase 24.15 (EC. 3.4.24.15), endopeptidase 24.16 (EC. 3.4.24.16), endothelin converting enzyme, angiotensin converting enzyme or similar peptidases. The invention is not limited to these enzymes.

As used herein, "amyloid peptide" includes beta or gamma amyloid peptides. Preferably, the peptide is amyloid beta peptide. More preferably, the beta peptide is $A\beta_{1-40}$ or $A\beta_{1-42}$. Most preferably, the beta peptide is $A\beta_{1-42}$.

As used herein, "selectable marker" includes a gene product that is expressed by a cell that stably maintains the introduced DNA, and causes the cell to express an altered phenotype such as morphological transformation, or an enzymatic activity. Isolation of cells that express a transfected gene is achieved by introduction into the same cells a second gene that encodes a selectable marker, such as one having an enzymatic activity that confers resistance to an antibiotic or other drug. Examples of selectable markers include, but are not limited to, thymidine kinase, dihydrofolate reductase, aminoglycoside phosphotransferase, which confers resistance to aminoglycoside antibiotics such as kanamycin, neomycin and geneticin, hygromycin B phosphotransferase, xanthine-guanine phosphoribosyl transferase, CAD (a single protein that possesses the first three enzymatic activities of de novo uridine biosynthesis—carbamyl phosphate synthetase, aspartate transcarbamylase and dihydroorotase), adenosine deaminase, and asparagine synthetase (Sambrook et al. *Molecular Cloning*, Chapter 16. 1989), incorporated herein by reference in its entirety.

As used herein, a "promoter" can be any sequence of DNA that is active, and controls transcription in an eucaryotic cell. The promoter may be active in either or both eucaryotic and procaryotic cells. Preferably, the promoter is active in mammalian cells. The promoter may be constitutively expressed or inducible.

As used herein, the term "biologically active" in reference to a nucleic acid, protein, protein fragment or derivative thereof is defined as an ability of the nucleic acid or amino acid sequence to mimic a known biological function elicited by the wild type form of the nucleic acid or protein.

As used herein, the term "maintenance", when used in the context of liposome delivery, denotes the ability of the introduced DNA to remain present in the cell. When used in other contexts, it means the ability of targeted DNA to remain present in the targeted cell or tissue so as to impart a therapeutic effect.

The present invention discloses ex vivo and in vivo techniques for delivery of a DNA sequence of interest to the brain tissue cells of the mammalian host. One of the ex vivo techniques involves culture of cells, in vitro transfection of the DNA sequence, DNA vector or other delivery vehicle of interest into the cells, followed by transplantation of the modified cells to the target joint of the mammalian host, so as to effect in vivo expression of the gene product of interest.

It will be understood by the artisan of ordinary skill that the preferred source of cells for treating a human patient is the patient's own tissue cells, such as autologous brain hippocampal or cortical cells or even fibroblasts.

As an alternative to the in vitro manipulation of cells, the gene encoding the product of interest is introduced into liposomes and injected directly into the area of the brain, where the liposomes fuse with the brain tissue cells, resulting in an in vivo gene expression of the amyloid peptide inhibiting enzyme.

As an additional alternative to the in vitro manipulation of brain tissue cells, the gene encoding the product of interest is introduced into the area of the brain as naked DNA. The naked DNA enters the brain tissue cell, resulting in an in vivo gene expression of the amyloid peptide inhibiting enzyme.

A further embodiment of the present invention includes employing as the gene a is gene capable of encoding an amyloid peptide inactivating enzyme or a biologically active derivative or fragment thereof, and employing as vector any DNA vector known to one of ordinary skill in the art capable of stable maintenance within the targeted cell or tissue upon delivery, regardless of the method of delivery utilized.

One such method is the direct delivery of the DNA vector molecule, whether it be a viral or plasmid DNA vector molecule, to the target cell or tissue. This method also includes employing as the gene a gene capable of encoding an amyloid peptide inactivating enzyme or biologically active derivative or fragment thereof.

Another embodiment of this invention provides a method for introducing at least one gene encoding a product into at least one cell for use in treating the mammalian host. This method includes employing non-viral means for introducing the gene coding for the product into the brain tissue cell. More specifically, this method includes a liposome encapsulation, calcium phosphate coprecipitation, electroporation, or DEAE-dextran mediation, and includes employing as the gene a gene capable of encoding an amyloid peptide inactivating enzyme or biologically active derivative or fragment thereof, and a selectable marker, or biologically active derivative or fragment thereof.

Another embodiment of this invention provides an additional method for introducing at least one gene encoding a product into at least one cell of a brain tissue for use in treating the mammalian host. This additional method includes employing the biologic means of utilizing a virus to deliver the DNA vector molecule to the target cell or tissue. Preferably, the virus is a pseudovirus, the genome having been altered such that the pseudovirus is capable only of delivery and stable maintenance within the target cell, but not retaining an ability to replicate within the target cell or tissue. The altered viral genome is further manipulated by recombinant DNA techniques such that the viral genome acts as a DNA vector molecule which contains the heterologous gene of interest to be expressed within the target cell or tissue.

A preferred method of the present invention involves direct in vivo delivery of an amyloid peptide inhibiting enzyme gene to the brain tissue of a mammalian host through use of either an adenovirus vector, adeno-associated virus (AAV) vector, lentivirus, or herpes-simplex virus (HSV) vector, or other viral vectors currently in development. In is other words, a DNA sequence of interests encoding a functional amyloid peptide inhibiting enzyme or enzyme fragment is subcloned into the respective viral vector. The amyloid peptide inhibiting enzyme gene containing viral vector is then grown to adequate titer and directed into the brain, preferably by cortical or hippocampal injection.

Direct brain tissue injection of a DNA molecule containing the gene of interest results in transfection of the recipient brain tissue cells and hence bypasses the requirement of removal, in vitro culturing, transfection, selection, as well as transplanting the DNA vector containing neuronal cells or fibroblasts to promote stable expression of the heterologous gene of interest.

Direct brain tissue injection of an amyloid peptide inhibiting enzyme through a brain pump represents yet another alternative method.

Still another alternative is to use pharmacological agents to induce synthesis of the endogenous gene encoding the amyloid peptide inhibiting enzyme. Such a pharmacological substance may be a compound that "up regulates" or enhances the expression of the amyloid peptide inhibiting enzyme. The pharmacological agent may bind to the regulatory region of the gene encoding the enzyme and thus activate its gene expression. Thus, the compound may be a transcriptional activator of the gene encoding the enzyme. Or, the compound may have a regulatory effect post transcriptionally in, for example, stabilizing the amyloid peptide inhibiting enzyme structure.

Still another alternative is to use pharmacological agents to increase the activity of the amyloid peptide inhibiting enzyme. Such a pharmacological substance may be a compound that enhances the activity of the amyloid peptide inhibiting enzyme. Without wishing to be bound by theory, the pharmacological agent may bind to the enzyme and thus increase its activity.

The pharmacological agent may be placed in pharmaceutically acceptable excipient or carrier and administered to a person or individual in need thereof. Depending on the specific clinical status of the disease, administration can be made via any accepted systemic delivery system, for example, via oral route or parenteral route such as intravenous, intramuscular, subcutaneous or percutaneous route, or vaginal, ocular or nasal route, in solid, semi-solid or liquid dosage forms, such as for example, tablets, suppositories, pills, capsules, powders, solutions, suspensions, cream, gel, implant, patch, pessary, aerosols, collyrium, emulsions or the like, preferably in unit dosage forms suitable for easy administration of fixed dosages. The pharmaceutical compositions will include a conventional carrier or vehicle and the pharmacological compound and, in addition, may include other medicinal agents, pharmaceutical agents, carriers, adjuvants, and so on.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, and so on.

The compounds of this invention are generally administered as a pharmaceutical composition comprising a pharmaceutical vehicle in combination with the pharmacological compound. The amount of the drug in a formulation can vary within the full range employed by those skilled in the art, e.g., from about 0.01 weight percent (wt %) to about 99.99 wt % of the drug based on the total formulation and about 0.01 wt % to 99.99 wt % excipient.

The preferred mode of administration, for the conditions mentioned above, is oral administration using a convenient daily dosage regimen which can be adjusted according to the degree of the complaint. For said oral administration, a pharmaceutically acceptable, non-toxic composition is formed by the incorporation of the selected pharmacological compound in any of the currently used excipients, such as, for example, pharmaceutical grades of mannitol lactose, starch, magnesium stearate, sodium saccharine, talc, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt % and 99.99 wt % of the active compound according to this invention.

Preferably the compositions will have the form of a sugar coated pill or tablet and thus they will contain, along with the active ingredient, a diluent such as lactose, sucrose, dicalcium phosphate, and the like; a disintegrant such as starch or derivatives thereof; a lubricant such as magnesium stearate and the like; and a binder such as starch, polyvinylpyriolidone, acacia gum, gelatin, cellulose and derivatives thereof, and the like.

It is understood that by "pharmaceutical composition", it is meant that the pharmacological compound is formulated into a substance that is to be administered purposefully for inactivating the amyloid protein. The mode of action is believed to be by cleavage of the amyloid inactivating protein. However, it is understood that the pharmacological compound per se will not have a toxic effect, and by "pharmaceutical composition", it excludes those compositions that are used to administer to individuals as test compounds for a purpose other than as an inducer of inactivation of the amyloid protein. In the first aim of this application we characterize the ability of insulysin and neprilysin to act as neuroprotective agents and determine if insulysin and neprilysin can prevent β-amyloid deposition. The second objective is to engineer insulysin so as to either have it secreted from cells or to have it expressed on the plasma membrane. Neprilysin is normally expressed on the cell surface and can be engineered to be secreted. Viral vectors are used to express insulysin and neprilysin in hippocampal and cortical neurons to show that these cells become resistant to the neurotoxic effects of Aβ peptides. The third objective is to express these constructs in an amyloid protein precursor (AβPP) transgenic mouse that expresses the human AβPP protein with the Swedish and Indiana mutations under the control of the platelet-derived growth factor (PDGF) B chain promoter, and designated as PDGF-APP$_{Sw, Ind}$ mice [A. Y. Hsia, E. Masliah, L. McConlogue, G. Q. Yu, G. Tatsuno, K. Hu, D. Kholodenko, R. C. Malenka, R. A Nicoll, L. Mucke L. *Plaque-independent disruption of neural circuits in Alzheimer's disease mouse models*. Proc. Natl. Acad. Sci. 96 (1999) 3228-3233.] or similar mammalian models of AD. We test this gene therapy approach to see if insulysin (IDE) and neprilysin (NEP) prevents plaque formation. In addition we will test whether these or other amyloid inactivating peptidases promote the dissolution of preformed amyloid plaques. The application is also directed to using gene therapy and pharmacological agents to treat Alzheimer's patients.

The balance between the anabolic and catabolic pathways in the metabolism of the Aβ peptides is a delicate one. Although considerable effort has focused on the generation of the Aβ peptides, until recently considerably less emphasis has been placed on the clearance of these peptides. Removal of extracellular Aβ appears to proceed through two general mechanisms; cellular internalization and extracellular degradation by neuropeptidases. Apparently neither of these mechanisms is adequate in Alzheimer's disease. Interest in the mechanism of cellular internalization stems from the apparent involvement of apolipoprotein B and α-2-macroglobulin in this process (Narita et al. (1997) *J. Neurochem* 69:1904-1911; Hughes et al. (1998) *Proc Natl Acad Sci USA* 95:3275-3280; Kang et al. (1997) *Neurology* 49:56-61; Blacker et al. (1998) *Nat Genet* 19:357-360).

We have expressed a His$_6$-tagged version of rat insulysin (insulin degrading enzyme, IDE) in Sf9 cells using the baculovirus expression system. The purified recombinant insulysin is fully active either with the His$_6$-tag removed by cleavage at a TEV protease site or with the His$_6$-tag intact. This purified recombinant insulysin has been used to analyze the cleavage of Aβ$_{1-40}$ and, Aβ$_{1-42}$ using MALDI-TOF and EMSI mass spectrometry to identify cleavage products. These experiments showed cleavage of both Aβ$_{1-40}$ and Aβ$_{1-42}$ at the His$^{13}$-His$^{14}$, His$^{14}$-Gln$^{15}$, and Phe$^{19}$-Phe$^{20}$ bonds.

Cleavage of both Aβ$_{1-40}$ and Aβ$_{1-42}$ by the recombinant insulysin was shown to initially occur at the His$^{13}$-His$^{14}$, His$^{14}$-Gln$^{15}$, and Phe$^{19}$-Phe$^{20}$ bonds. This was followed by a slower cleavage at the Lys$^{28}$-Gly$^{29}$, Val$^{18}$-Phe$^{19}$ and Phe$^{20}$-Ala$^{21}$ positions. None of the products appeared to be further metabolized by insulysin. Using a rat cortical cell system, the action of insulysin on Aβ$_{1-40}$ and Aβ$_{1-42}$ was shown to eliminate the neurotoxic effects of these peptides. Insulysin was further shown to prevent the deposition of Aβ$_{1-40}$ onto a synthetic amyloid. Taken together these results suggest that the use of insulysin to hydrolyze Aβ peptides represents an alternative gene therapeutic approach to the treatment of Alzheimer's disease.

The cleavage products observed with insulysin indicate distinct cleavage events and not products derived from secondary cleavage of an initial product. That is, no fragment was observed lacking an intact N-terminus, the C-terminal fragment corresponding to each N-terminal fragment was seen in all but one case, and products increased with an increasing concentration of insulysin.

Neuronal cell cultures are susceptible to the toxic effects mediated by Aβ$_{1-40}$ and Aβ$_{1-42}$. We have used this neuronal cell culture system to establish that the products of the insulysin dependent cleavage of Aβ$_{1-40}$ and Aβ$_{1-42}$ produces products that are not in is themselves neurotoxic. This is an important point if one were to consider the use of insulysin in the treatment of Alzheimer's disease.

Related to cellular toxicity, Aβ peptides are able to deposit onto an existing matrix of peptides in what is thought to lead to an increase in the size of senile plaques and consequently to the progression of Alzheimer's disease. In a model system, Esler et. al. (Esler et al. (1997) *Nat Biotech* 15:268-263) have shown that the deposition of Aβ$_{1-40}$ onto a preformed synthaloid matrix mimics the in vivo deposition of Aβ peptides onto the brain cortex. Using this model, we have shown that insulysin (insulin degrading enzyme) cleavage of Aβ$_{1-40}$ prevents the deposition of the Aβ peptides onto the synthaloid. This suggests that insulysin may be able to prevent the formation and growth of senile plaques in Alzheimer's disease patients.

In summary we have established that the insulysin dependent cleavage of the Aβ peptides leads to the loss of both their neurotoxic properties as well as their ability to contribute to plaque formation and growth. The use of insulysin and other peptidases to degrade extracellular Aβ peptides represents a new approach toward the treatment of Alzheimer's disease.

An objective of this patent application is to further describe and characterize the ability of insulysin to act as a neuroprotective agent. We measure the ability of insulysin to protect cultured hippocampal and cortical cells from the toxic effects of Aβ$_{1-40}$ and Aβ$_{1-42}$. For these experiments primary hippocampal and cortical cells are obtained from 18 day rat embryos as described by Mattson et al. (M. P. Mattson et al. (1995) *J. Neurochem.* 65, 1740-1751) and initially cultured for seven days in Eagles MEM supplemented with fetal bovine serum, KCl, pyruvate, and gentamicin as described by Lovell et al (M. A. Lovell et al. (1999) *Brain Res.* 823, 88-95). Prior to use, the cells are transferred to Locke's media and dispersed in 96 well plates at a density of ~10$^5$ cells/well. Cells are then treated in triplicate with varying concentrations of Aβ$_{1-40}$ and Aβ$_{1-42}$ (1 to 25 Z for up to 48 hrs. Toxicity of the Aβ peptides are quantitated at various times by measuring MTT oxidation and LDH release (C. Behl et al. (1994) *Cell* 77, 817-827) using assay kits from Promega Corp. (Promega CYTO-TOX96® Non-Radioactive Cytotoxicity Assay Kit), a lactate dehydrogenase (LDH) release kit). Another set of cultures will have added to them 5 to 500 ng of purified insulysin previously dialyzed into Locke's media and filter sterilized. We have previously established that insulysin is fully active in Locke's media under cell culture conditions for several days. As a control, insulysin inactivated by removal of its zinc cofactor by treatment with o-phenanthroline, and then dialyzed to remove the o-phenanthroline, are used. Another control will have insulysin added to the cultured cells in the absence of Aβ peptides.

A variation of this protocol is to pre-aggregate the Aβ peptides prior to their addition to the cultured cells. For aggregation, Aβ peptide is incubated in Locke's media and the formation of aggregates followed by measuring an increase in turbidity at 400 nm. The Aβ peptide is allowed to maximally aggregate before use. The aggregated Aβ peptide is then added to the primary cultures as noted above in the presence or absence of insulysin, and toxicity determined as indicated above. Under this experimental condition insulysin will be protective if it can hydrolyze Aβ in the aggregated state or if aggregation is rapidly reversible and the free Aβ can be broken down by insulysin.

The next set of experiments utilizes a "more physiological" Aβ deposition assay in which physiological concentrations (~$10^{-9}$ M of $^{125}$I-Aβ are deposited onto a preformed synthetic amyloid (synthaloid) in a 96 well plate (W. P. Esler et al. (1999) *Meth. In Enz.* 309, 350-374). The assay is readily quantitated by measuring the 12 deposited onto the plate. The 96 well plates containing synthaloid are available commercially from QCB/BioSource and $^{125}$I-Aβ is available from Amersham. This assay is used to determine if insulysin can prevent $Aβ_{1-40}$ and $Aβ_{1-42}$ deposition. Varying amounts of insulysin are added to incubation mixtures containing $^{125}$I-Aβ (100 μM) in Tris buffer and the rate of radiolabeled Aβ deposition in the presence and absence of insulysin are compared. Ortho-phenanthroline treated insulysin is used as a control. Experiments suggest that insulysin hydrolysis products of $Aβ_{1-40}$ do not deposit onto the synthaloid.

A variation of this assay is used to see if insulysin can release newly deposited Aβ. In this assay $^{125}$I-Aβ is deposited onto preformed synthaloid for 2-4 hrs, free Aβ is washed away, and then buffer is added with or without insulysin. The supernatant is counted at various times to see if the newly deposited Aβ is solubilized. This assay is also used to see if insulysin can "dissolve" preformed amyloid plaques. In these experiments $^{125}$I-Aβ is used during the preparation of the synthaloid which will permit it to become an integral part of the synthetic amyloid aggregate. Insulysin or control inactive insulysin is added to the pre-formed $^{125}$I-Aβ synthaloid and incubated for varying lengths of time. The amount of $^{125}$I released into the media is then measured. As noted above $^{125}$I release occurs if insulysin can act directly on the Aβ fibrils or if there is a dynamic equilibrium between free Aβ and Aβ in the plaque.

Taken together these in vitro experiments demonstrate the usefulness of insulysin and neprilysin to protect against both the neurotoxicity of Aβ and to prevent Aβ from being deposited onto amyloid plaques.

As disclosed herein, we have found, unexpectedly, that estrogen can increase the expression of neprilysin in the brain. The largest increase is in the expression of type 1 neprilysin mRNA, which is the predominant neprilysin transcript in brain. Estrogen also increased the expression of type 2 neprilysin mRNA in brain. These observations provide the basis for screening assays to identify additional compounds that modulate expression of amyloid peptide inactivating enzymes, including, for example, one or more of the following: neprilysin, insulysin, endopeptidase 24.15 (E.C. 3.4.24.15), endopeptidase 24.16 (E.C. 3.4.24.16), endothelin converting enzyme, angiotensin converting enzyme, and similar peptidases.

In certain embodiments, the screening methods involve a step of assessing the effect of a test compound on expression of an amyloid peptide inactivating enzyme (APIE) in a nervous system cell or nervous system-derived cell that expresses an APIE. In other embodiments, the screening methods involve a step of assessing the effect of an estrogen or analog thereof on expression of an APIE. In other embodiments, the screening methods involve the step of assessing the effect of a test compound on expression of type 1 or type 2 neprilysin mRNA. In further embodiments, the screening methods involve the step of assessing the effect of a test compound on expression of a nucleotide coding sequence contained within a nucleotide sequence containing type 1, type 2 or type 3 neprilysin mRNA regulatory element(s). The APIE or neprilysin can be of any origin, such as mammalian, human, rat, mouse, or other species.

As used herein, the term "assessing" with respect to "expression" of a nucleic acid molecule, such as an APIE mRNA, neprilysin mRNA, type 1, type 2 or type 3 neprilysin mRNA, or a nucleotide coding sequence contained within a nucleotide sequence containing type 1 or type 2 neprilysin mRNA regulatory element(s), refers to the process of determining, either qualitatively or quantitatively, the expression of the nucleic acid molecule. Such a process can involve any direct or indirect determination of the type and/or amount, or relative amount, of the nucleic acid, e.g., the reference mRNA, using techniques known to those of skill in the art. For example, the type or amount of a particular mRNA can be directly determined or measured, or the amount of protein or activity of the protein encoded by a particular mRNA can be determined or measured as an indirect assessment of nucleic acid expression.

A compound that modulates expression relative to a suitable control, such as a sample that is untreated, or which is treated with a vehicle, is identified. Expression generally refers to the generation and maintenance of a transcript or mRNA, such as an mRNA that encodes a protein. As used herein, the term "modulates" indicates that the compound alters expression, such as by, for example, increasing, decreasing and/or altering the timing or pattern of expression of the reference molecule. Such an alteration can be a result of the compound acting on any molecule (e.g. DNA, transcriptional machinery, mRNA) or process (e.g. initiation, elongation, stabilization, etc.) involved in expression. For example, the compound can modulate expression by acting directly as a transcriptional regulator (e.g. an enhancer or silencer). Alternatively or additionally, the compound can modulate expression by modulating the activity of a transcriptional regulator (e.g. by binding to a steroid receptor that acts as a transcriptional regulator; by inhibiting binding of a transcriptional regulator to its regulatory element, etc.). In another example of modulation of expression, a compound can act to increase or decrease the stability of an mRNA molecule. A compound that "enhances" expression can be a compound that increases expression by any detectable amount, such as an increase of at least 1%, 2.5%, 5%, 10%, 25%, 50%, or more. A compound that "inhibits" expression can be a compound that decreases expression by any detectable amount, such as an decrease of at least 1%, 2.5%, 5%, 10%, 25%, 50%, or more. In a particular embodiment, an identified compound is one that can modulate expression to a statistically significant extent relative to a control. In particular embodiments of the screening methods, an identified compound is one that enhances expression of an mRNA. In particular embodiments, such a compound is a steroid or analog thereof, and, in particular embodiments, is an estrogen or analog thereof.

General methods of determining mRNA and protein expression and enzyme activity are well known in the art and described, for example, in Sambrook and Russell (2000) "Molecular Cloning: A Laboratory Manual" Cold Spring Harbor Laboratory Press; Ausubel et al. (eds.) (current edition) "Current Protocols in Molecular Biology" John Riley & Sons; and in Harlow and Lane (1998) "using Antibodies: A Laboratory Manual" Cold Spring Harbor Laboratory Press. Such methods can be adapted to determine the expression of any mRNA or protein of interest.

For example, methods of determining mRNA abundance can involve hybridization of the target nucleic acid molecule to detectably labeled probes (e.g. Northern and Southern blots and various array-based methods). Other methods can involve hybridization of the target nucleic acid molecule to primers, which can then be extended by polymerases (e.g. PCR, RT-PCR, primer extension and sequencing-based methods). The hybridization or extension products, or their derivatives (e.g. products produced by further cleavage, transcription, translation and/or labeling of the hybridization or extension products), are then identified by a suitable analytical method known in the art, such as gel electrophoresis and blotting, mass spectrometry, fluorescent scanning, and the like.

In certain embodiments, the expression of neprilysin mRNA is assessed. As used herein, "neprilysin mRNA" refers to any or all types (e.g., type 1, 2 (2a or 2b) and 3) of neprilysin mRNA, from any species, expressed by any cell.

Figure 18:
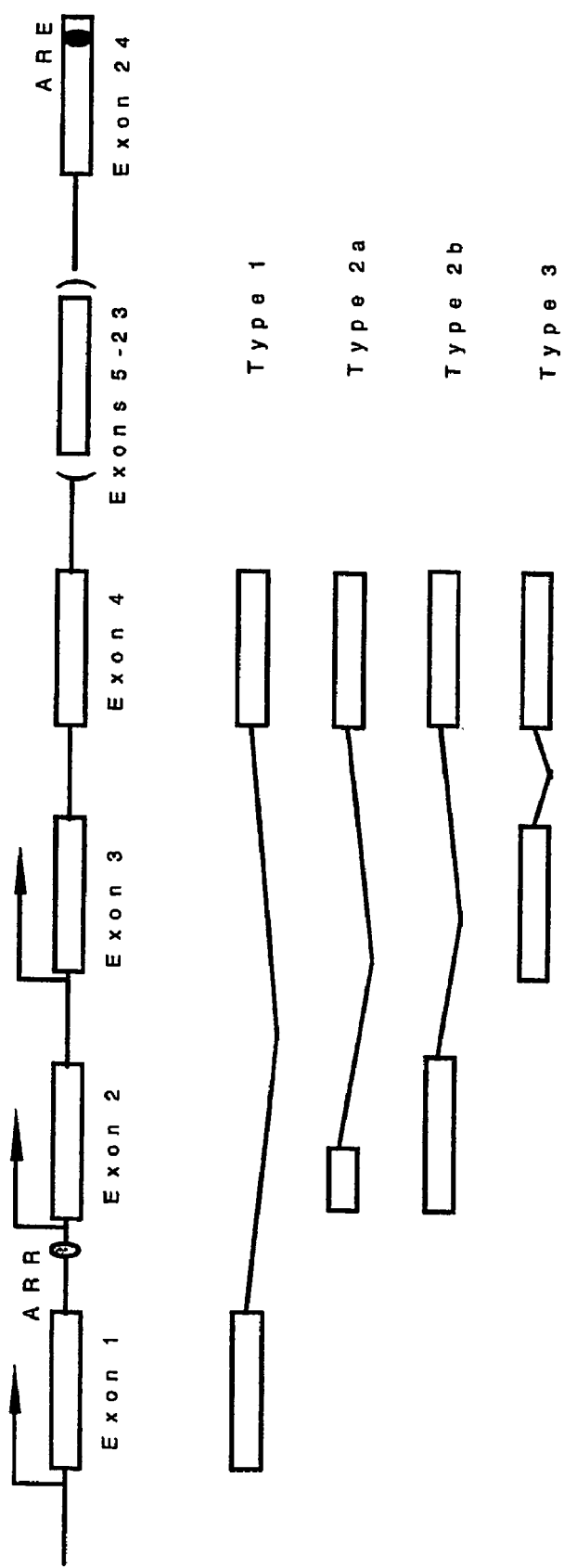
FIG. 18 is a scheme showing the neprilysin gene and its mRNA transcripts. The neprilysin gene is composed of 24 exons of which exons 1, 2, and 3 are non-coding exons and exon 4 is the first coding exon. the androgen response element (ARE) is located in the last coding exon as part of the 3' untranslated sequence. The androgen response region (ARR) is located upstream of exon 2 within the second intron. There are three promoters indicated by arrows. The four neprilysin mRNA transcripts are dervice by alternative splicing as illustrated.

In certain embodiments, the expression of type 1, type 2 or type 3 neprilysin mRNA is assessed. As used herein, "type 1 neprilysin mRNA" refers to mRNA containing exon 1 of neprilysin. Likewise, "type 2 neprilysin mRNA" refers to mRNA containing all or a portion of exon 2 of neprilysin (type 2b and type 2a, respectively), and "type 3 neprilysin mRNA" refers to mRNA containing exon 3 of neprilysin. The sequences and exon/intron boundaries of neprilysin are known in the art, and thus probes and primers can be generated to detect any or all types of neprilysin mRNA. A schematic of neprilysin gene structure is shown in FIG. 18. Examples of nucleotide sequences containing neprilysin type 1 mRNA sequence (GenBank accession no. NM_000902), type 2a mRNA sequence (GenBank accession no. NM_007288), type 2b mRNA sequence (GenBank accession no. NMK_007289) and exon 3 sequence (GenBank accession no. U26729) are known in the art. As described in Example 15, when neprilysin mRNA abundance is assessed, probes can be generated that specifically hybridize to nucleotide sequences that are specific to types 1, 2 (2 a and/or 2b) or 3 mRNA, or that are common to all types of neprilysin mRNA.

Methods of determining protein abundance can conveniently involve the use of antibodies (e.g. monoclonal or polyclonal antibodies) or other specific binding agents, which can be generated against either an APIE or a reporter protein by methods known in the art. Exemplary methods for determining protein abundance that involve the use of antibodies include immunoprecipitation (optionally in combination with electrophoretic separation or a denaturing or non-denaturing gel or mass spectroscopic analysis), western hybridization, immunocytochemistry, fluorescence resonance energy transfer (FRET)-based methods, and various formats of enzyme-linked immunosorbent assays (ELISA).

Methods of determining expression based on reporter gene activity are also known in the art. Using standard recombinant DNA approaches, any sequence of interest, such as neprilysin mRNA regulatory element(s), can be operatively linked to a coding nucleotide sequence, which may encode neprilysin or a reporter. As used herein, the term "reporter" refers to a heterologous nucleotide sequence whose transcription, translation or polypeptide activity can be detected, and optionally quantified, when the sequence is operatively linked to suitable regulator(s) of RNA transcription. Reporter sequences and methods of detecting and quantifying their transcription, translation or polypeptide activity, are well known in the art.

Exemplary reporters encode proteins that exhibit enzymatic activity, confer drug resistance, exhibit fluorescence or luminescence, and the like. Specific examples of reporters are beta-lactamase, luciferase, chloramphenicol acetyltransferase, green fluorescent protein and beta-galactosidase.

In certain embodiments, expression of mRNA which is transcribed from a nucleic acid containing type 1, type 2 (2a or 2b) or type 3 neprilysin mRNA regulatory element(s) is assessed. As used herein, the term "neprilysin regulatory element" refers to any cis sequence that modulates the amount, rate or specificity of transcription of neprilysin mRNA, such as a type 1, type 2 (2a and/or 2b) or type 3 neprilysin mRNA, including promoters, enhancers, silencers, transcription factor binding sites and untranslated nucleotide sequences, e.g., 5' and 3' untranslated sequences, and the like. Untranslated sequence regions (UTRs), e.g., 5' and 3'UTRs, can function to regulate gene transcription, e.g., patterns and levels of transcription [see, e.g., Smicun et al. (1998) Eur. J. Biochem. 251:704-715]. For example, the 5' untranslated region of a gene can influence the activity of an element of the gene promoter and thus the expression of the mRNA (e.g. level or timing of expression).

Figure 19:
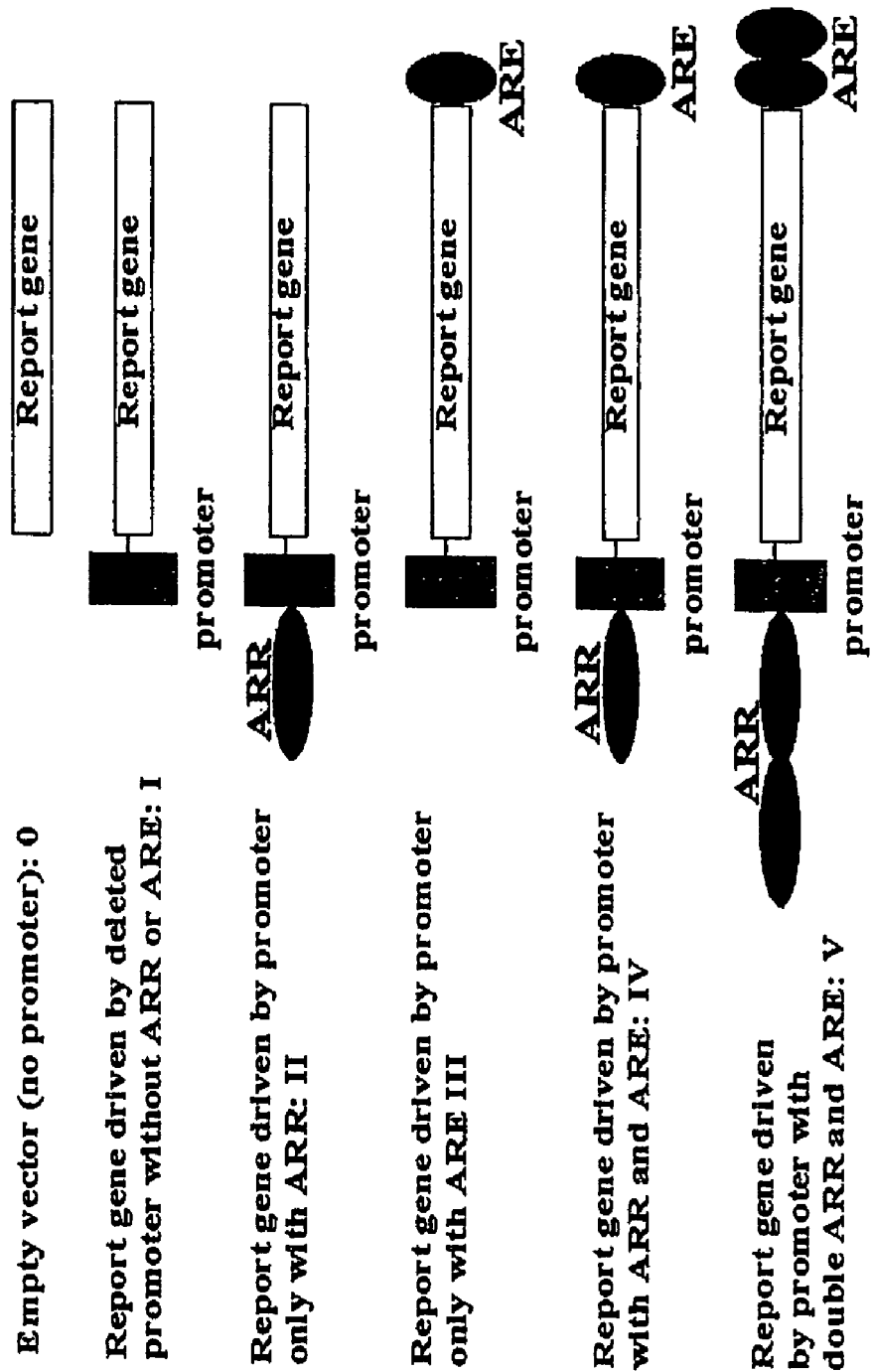
FIG. 19 illustrates exemplary neprilysin constructs.

An exemplary type 1 neprilysin regulatory element is the type 1 promoter, which is contained within about 85 nucleotides upstream of exon 1. A type 1 neprilysin enhancer-like sequence is located within a 22-bp fragment located at −136 to −115 (Li and Hersh (1998) Arch. Biochem. Biophys. 358: 189-195). Additional type 1 neprilysin mRNA regulatory sequences may be contained in exon 1, such as the 5' UTR of exon 1, of the neprilysin gene. An exemplary type 2 neprilysin regulatory element is the type 2 promoter, which is contained within the region of −263 to +147 of the human neprilysin gene relative to the major initiation of transcription site (see, e.g., Ishimaru et al. (1995) Blood 85:3199 and Ishimaru et al. (1997) Blood 89:4136-4145). At least three transcription factor binding sites have been identified in the type 2 promoter at sites located at −145 to −116, −93 to −53 and −52 to −23 (see Ishimaru et al. (1997) Blood 89:4136-4145). Additional type 2 neprilysin mRNA regulatory sequences may be contained in exon 2 (e.g., the type 2a and type 2b regions), such as the 5' UTR of exon 2, of the neprilysin gene. Type 3 neprilysin mRNA regulatory sequences may also be contained in exon 3, such as 5' UTR of exon 3, of the neprilysin gene. Examples of neprilysin mRNA 5' UTRs are also described in Li et al. [(1995) J. Biol. Chem. 270:5723-5728]. Other exemplary type neprilysin regulatory elements include steroid responsive elements, such as the androgen response element (ARE) located in the 3' untranslated region of the gene, and the androgen response region (ARR) located between exon 1 and exon 2 (Shen et al. (2000) Mol. Cell. Endocrinol. 170:131-142). Additional potential regulatory elements can be identified, for example, using computer programs such as TRANSFAC (Wingender et al. (2001) Nucleic Acids Res. 29:281-283) and TFSEARCH (www.cbrc.jp/research/db/TFSEARCH.html). Methods of generating suitable constructs that contain one or more neprilysin regulatory element(s) employ standard recombinant DNA technology. Exemplary constructs are shown in FIG. 19.

In certain embodiments, expression of an APIE mRNA, such as neprilysin mRNA, is determined in a nervous system cell or nervous system-derived cell. As used herein, the term "nervous system or nervous system-derived cell" refers to a cell present in, obtained from, or derived in culture from, any region of the central or peripheral nervous system of an animal, including the brain (e.g. hippocampus, cortex, thalamus/striatum, cerebellum, etc.), spinal cord, cerebrospinal fluid and peripheral nerves of an animal. Animals include, for example, mammals, humans, non-human primates, rodents (e.g. rats and mice) and other laboratory animals. Nervous system or nervous system-derived cells derived in culture include primary cells and cell lines, such as neurons, glial cells and astrocytes and their progenitors and progeny, which may be transformed or untransformed. Example 15 describes an exemplary method of determining expression of neprilysin mRNA in hippocampus. Similar methods can be used to determine expression of other APIEs in nervous system cells or nervous system-derived cells.

In certain embodiments, the nervous system cells or nervous system-derived cells express steroid receptors, such as estrogen or androgen receptors. Those skilled in the art can readily determine whether a given cell expresses endogenous steroid receptors, either by assessing steroid receptor expression or activity. In instances where a cell does not express sufficient levels of endogenous steroid receptors, an expression construct encoding a suitable steroid receptor can be introduced into the cell by standard methods.

As disclosed herein, we have also found, unexpectedly, that beta endorphin, dynorphin and bradykinin peptides can increase insulysin enzymatic activity. These observations provide the basis for screening assays to identify additional compounds that 15: enhance the activity of amyloid peptide inactivating enzymes, including, for example, one or more of the following: insulysin, neprilysin endopeptidase 24.15 (E.C. 3.4.24.15), endopeptidase 24.16 (E.C. 3.4.24.16), endothelin converting enzyme, angiotensin converting enzyme, and similar peptidases. The APIE can be of any origin, such as mammalian, human, rat, mouse, or other species.

In one embodiment, the screening methods involve assessing the effect of a test compound on activity of an amyloid peptide inactivating enzyme (APIE). In particular embodiments, the method involves assessing the effect of a test compound on activity of insulysin or neprilysin. As used herein, the term "assessing" with respect to "activity" of an APIE, refers to the process of determining, either qualitatively or quantitatively, the amount of a biological activity of an APIE. A compound that enhances activity relative to a suitable control, such as a sample that is untreated, or which is treated with a vehicle, is identified. A compound that "enhances" activity can be a compound that increases activity by any detectable amount, such as an increase of at least 1%, 2.5%, 5%, 10%, 25%, 50%, or more. Such an increase in activity can be a result of the compound acting by any mechanism. For example, the compound can affect the affinity of the enzyme for its substrate, the affinity of the enzyme for the product, the rate of substrate cleavage, the stability of the enzyme, or the like. In a particular embodiment, an identified compound can be one that increases activity to a statistically significant extent relative to a control.

Methods of assessing activity of an APIE can take advantage of any biological activity of the APIE, including the ability of an APIE to cleave a substrate. For example, as disclosed herein, insulysin cleaves amyloid beta peptides initially between the $His^{13}$-$His^{14}$, $His^{14}$-$Gln^{15}$ and $Phe^{19}$-$Phe^{20}$ bonds, and also cleaves insulin, glucagons and atrial naturitic peptide. The sites of cleavage of other APIE enzymes are known in the art or can be determined by methods similar to those described herein for identification of insulysin cleavage of Aβ. Thus, APIE activity assays can involve the step of measuring the cleavage of an Aβ peptide, or of a synthetic peptide containing amino acids flanking a cleavage site of an Aβ peptide. Either the reduction in the amount of substrate, or the increase in the amount of one or more cleavage products, can be assessed in such assays.

Methods such as HPLC or mass spectrometry can be used to directly monitor substrates and cleavage products. Alternatively, an APIE substrate sequence can be detectably labeled in such a manner that the substrate and product have qualitatively or quantitatively different properties. For example, an APIE substrate sequence can be flanked by a donor fluorescent moiety and an acceptor quencher moiety. The uncleaved substrate has low fluorescence due to quenching of the donor by the acceptor. Upon cleavage by the APIE, the donor and acceptor moieties are no longer in proximity, and the donor fluoresces strongly because it is no longer quenched. The amount of donor fluorescence is directly proportional to the APIE activity. An exemplary peptide substrate containing donor and acceptor moieties and its use in peptidase activity assays, Abz-GGFLRKHGQ-EDDnp, is described in Example 17. Another fluorogenic assay is described in Example 16 using the peptide substrate glutaryl-Ala-Ala-Phe-4-methoxy-2-naphthylamide. In that assay, cleavage of the peptide substrate by a peptidase such as neprilysin yields Phe-4-methoxy-2-naphthylamide which in turn yields a fluorescent 4-methoxy-2-naphthylamine when cleaved by an aminopeptidase (see also Thompson et al. (2003) *Arch. Biochem. Biophys.* 413:236-242). Other assays for determining peptidase activity are well known in the art and can be adapted for use in assessing APIE activity, based on knowledge of the substrates and cleavage sites therein.

The screening assays described herein can involve contacting either an in vivo or in vitro sample with a test compound, and assessing expression or activity. Unless inconsistent with the nature of the method or specified otherwise, the term "sample" refers to a live organism (including a human subject, or a laboratory or veterinary animal), a tissue or body fluid therefrom, or extract thereof), a cell (such as a primary cell or cell line of any tissue origin) or extract thereof, extracellular medium or matrix or milieu, or isolated protein.

As used herein, "contacting" refers to bringing into association, either directly or indirectly, two or more substances. Contacting may occur in vivo, ex vivo or in vitro. A sample that is a human or other animal can be contacted with a compound, for example, by therapeutic or prophylactic administration of the compound. A sample that is a tissue, tissue extract or cell can be contacted with a compound, for example, by introduction of the compound into the culture medium. A sample that is a fluid, such as extracellular medium, can be contacted with a compound, for example, by admixing the compound with the fluid.

The screening methods and therapeutic methods described herein involve the use of compounds. As used herein, the term "compound" includes any biomolecule such as a peptide, polypeptide, peptidomimetic, saccharide, fatty acid, steroid, purine, pyrimidine, nucleic acid, derivative or analog thereof, and any such molecules in combination. Such biomolecules can be substantially purified, or can be present in a mixture, such as a cell extract or supernate. The term "compound" further includes synthetic or natural chemical compounds, such as simple or complex organic or inorganic molecules, metal-containing compounds, and the like. Also included are known pharmacological compounds, which optionally can be subjected to directed or random chemical modifications, such as acylation, alkylation, esterification, amidation, etc., to produce structural analogs. Test compounds or compounds suitable for use in the invention screening methods can optionally be contained in compound libraries. Methods for producing compound libraries by random or directed synthesis of a wide variety of organic compounds and biomolecules are known in the art, and include expression of randomized oligonucleotides and oligopeptides. Methods of producing natural compounds in the form of bacterial, fungal, plant and animal extracts are also known in the art. Additionally, synthetically produced or natural compounds and compound libraries can be readily modified through conventional chemical physical and biochemical means to produce combinatorial libraries. Compound libraries are also available from commercial sources.

In certain embodiments, the compounds are steroids, or steroid analogs. As used herein, the term "steroid" refers to structural derivatives of cholesterol or of retinoic acid, which generally contain the same cyclopentanophenanthrene ring as cholesterol or contain the core structure of Vitamin D. The term "steroid" includes all human, mammalian, other vertebrate, insect and plant steroids, as well as synthetic steroids. Major classes of mammalian steroid hormones include progestagens (progestational hormones), glucocorticoids (anti-stressing hormones), mineralcorticoids (Na+ uptake regulators), androgens (male sex hormones), and estrogens (female sex hormones). Exemplary steroids include pregnenolone, estrogen (e.g. 17 beta-estradiol), aldosterone, testosterone, androstenedione, progesterone, cortisol, deoxycortisol, corticosterone, dehydroepiandosterone, calcitriol, ecdysone and vitamin D.

The term "steroid analog" refers to a molecule that contains one or more structural differences relative to known steroids. For example, the degree of saturation of at least one bond in the cyclopentanophenanthrene ring can be changed (e.g., a single bond can be changed to a double or triple bond, or the converse), a bond can be removed, one or more carbon, oxygen or hydrogen atoms can be replaced with a different atom or a chemical moiety (e.g. a halogen, oxygen, nitrogen, sulfur, hydroxy, methoxy, alkyl, aryl, cycloalkyl, heterocycle, amine, amide, ketone, aldehyde, etc.), and the like. A steroid analog may possess one or more biological activities of the parent steroid, such as binding to, or activation of, the steroid receptor. Other types of derivatives of steroids that would be encompassed by the term "steroid analog" are known in the art. Exemplary estrogen analogs include, for example, tamoxifen, diethylstilbestrol, resveretrol, genestein, raloxifene, ICI-164384, and the like.

In certain embodiments, the compounds are peptides, or derivatives or analogs thereof. As used herein, a "derivative or analog" of a peptide includes molecules whose structure resembles or mimics the three-dimensional structure of a peptide. Such molecules may have one or a few chemical modifications relative to a peptide, or may have little chemical resemblance to a peptide. Peptide derivatives or analogs, for example, may include non-naturally occurring amino acids or amino acid analogs, altered chemical bonds, substitutions of atoms, and the like, relative to a peptide. Exemplary peptide derivatives or analogs useful in the methods described herein are derivatives or analogs of beta endorphin, dynorphin or bradykinin, or derivatives or analogs of other substrates of APIEs. Such molecules can be generated by those skilled in the art based on the predicted tertiary structure of these peptides.

Compounds used in the screening methods are referred to as "test compounds." A test compound identified by the screen as a "candidate compound" for use in reducing formation or growth of amyloid plaque or reducing amyloid peptide neurotoxicity can be further assessed with respect to particular effects on amyloid. For example, test compounds identified by the screening methods can be further assessed for their ability to reduce formation or growth of amyloid plaque, reduce amyloid peptide neurotoxicity, and/or treat Alzheimer's disease and other conditions associated with amyloid plaque formation and/or amyloid peptide neurotoxicity. A candidate compound may be a compound that can be directly used as a therapeutic compound, or may be a compound which, due to one or more undesirable pharmaceutical properties, cannot be directly used as a therapeutic compound, but which has the potential for use as a lead compound in the development of compounds with more acceptable pharmaceutical properties.

Compounds that modulate the expression of an APIE in a nervous system cell or nervous system-derived cell, modulate the expression of neprilysin mRNA, modulate the expression of type 1 or type 2 neprilysin mRNA, or modulate the expression of a nucleotide coding sequence contained within a nucleotide sequence containing neprilysin mRNA regulatory element(s), including, for example, type 1 or type 2 neprilysin mRNA regulatory element(s), can be used in reducing formation or growth of amyloid plaque or reducing amyloid peptide neurotoxicity, as well as in other therapeutic applications in which an increase or decrease in APIE expression, and, in particular, neprilysin expression, is desirable. For example, modulation of the expression of an APIE, such as neprilysin, can be applied in the treatment of cancer, including lung and prostate cancer.

In particular embodiments, such treatment can involve enhancing APIE expression. In other examples, modulation of the expression of an APIE, such as neprilysin, can be used in analgesic and anti-diarrheal applications and in the treatment of cardiomyopathies, heart failure and cardiovascular diseases and disorders. In particular embodiments, such applications can involve decreasing APIE expression. Likewise, compounds that enhance APIE activity, and, in particular insulysin or neprilysin activity, can also be used in reducing formation or growth of amyloid plaque or reducing amyloid peptide neurotoxicity, as well as in other therapeutic applications in which an increase in APIE, such as insulysin or neprilysin, activity is desirable. Examples of such applications include conditions involving dysregulation of insulin, e.g., obesity, and of the immune system.

Identified test compounds have additional utility in numerous research and development applications. For example, such compounds could be used to examine the molecular and/or physiological consequences of modulation of expression or activity of an is APIE in a cell or transgenic animal. Additional molecules whose expression or activity is modulated as a consequence of modulating APIE expression or activity can thereby be identified, such molecules in turn being targets for development of therapeutic compounds.

As used herein, "reducing formation or growth of amyloid plaque" refers to any delay or reduction in the initial formation of amyloid plaque, or any delay or reduction in the further growth of amyloid plaque, whether in a permanent or temporary manner. Such a delay or reduction can be due to enhanced cleavage of monomeric, oligomeric or aggregated amyloid peptides, which can result, for example, in a delay or reduction in fibril formation or deposition, or in an enhancement of degradation or clearance of amyloid plaque. Assays for determining whether a compound modulates formation or growth of amyloid plaque include the amyloid beta deposition assays described in Examples 3 and 8 herein, and the pre-aggregated amyloid beta degradation assay described in Example 11, herein. Other suitable assays are known in the art, and include visualization of amyloid deposits in brain sections, and brain imaging methods.

As used herein, "reducing amyloid peptide neurotoxicity" refers to any delay or reduction in the amount of toxicity to nervous system cells or nervous system-derived cells due to amyloid peptides. Such a delay or reduction can be due to enhanced cleavage of neurotoxic amyloid peptides, including Aβ40 and Aβ42, resulting in reduced levels of such peptides. Assays for determining whether a compound modulates neurotoxicity due to amyloid peptides include the cortical neuronal survival assay described in Example 9, herein, and the hippocampal neuronal cell survival assay described in Example 2, herein.

Alternative assays measure the levels of Aβ peptides that are considered to be neurotoxic. Sandwich ELISA assays are particularly suitable for assessing Aβ levels in tissues, cells and fluids (e.g. body fluids and extracellular media). In such assays, a first antibody (such as an Aβ42- or Aβ40-selective antibody) is used to capture the antigen in the sample, while the second antibody (such as a non-selective Aβ antibody) is used to detect the captured antigen. An alternative assay for assessing Aβ levels involves immunoprecipitation and mass spectrometric analysis. For example, Aβ peptides can be immunoprecipitated with a suitable antibody bound to a Sepharose column, eluted, and spotted onto NP2 CHIPS. Mass spectrometric analysis can be performed, for example, on a PBS II Protein Chip Reader (Ciphergen).

As used herein, "treating" with respect to Alzheimer's disease and other conditions associated with amyloid plaque formation and/or amyloid peptide neurotoxicity refers to any pharmaceutical use of a compound or composition in an individual having, or at risk or developing, symptoms or neuropathological features of Alzheimer's disease. The term encompasses pharmaceutical uses in which one or more of the symptoms or neuropathological features of the disease are ameliorated or otherwise beneficially altered, whether in a permanent or temporary manner, which can be attributed to or associated with administration of the compound or composition. The term also encompasses prophylactic uses in which the development of one or more of the symptoms or neuropathological features of the disease is prevented, delayed or reduced, whether in a permanent or temporary manner, which can be attributed to or associated with administration of the compound or composition.

Conditions associated with beta amyloid plaque formation and/or beta amyloid peptide neurotoxicity include Alzheimer's disease, Down syndrome, Parkinson's disease, diffuse Lewy body disease, progressive supranuclear palsy and Hereditary Cerebral Hemorrhage with Amyloidosis-Dutch Type (HCHWA-D), and other neurodegenerative disorders. The methods and compounds for reducing formation or growth of amyloid plaque or for reducing amyloid peptide neurotoxicity can be used to in connection with any of these conditions.

Symptoms of Alzheimer's disease are known in the art and include, for example, dementia, aphasia (language problems), apraxia (complex movement problems), agnosia (problems in identifying objects), progressive memory impairment, disordered cognitive function and altered behavior (including paranoia, delusions and loss of social appropriateness). Standardized clinical criteria for the diagnosis of AD and for the assessment of clinical symptoms have been established by NINCDS/ADRDA (National Institute of Neurological and Communicative Disorders and Stroke/Alzheimer's Disease and Related Disorders Association) (McKhann et al. (1984) Neurology 34:939-944).

Neuropathological features of Alzheimer's disease are also known in the art and include, for example, neuritic (senile) plaques, neurofibrillary tangles (NFTs), amyloid deposits in cerebral blood vessels (beta amyloid angiopathy) and neuronal loss.

Neuropathological criteria for the diagnosis of AD have been established by Consortium to Establish a Registry for Alzheimer's Disease (CERAD) (Mirra et al. (1991) Neurology 41:479-486).

Symptoms and neuropathological features of Down syndrome, Parkinson's disease, diffuse Lewy body disease, progressive supranuclear palsy and Hereditary Cerebral Hemorrhage with Amyloidosis-Dutch Type (HCHWA-D), and other neurodegenerative disorders are also known in the art.

An individual or subject that is "treated" with a compound can be a human or an animal model of Alzheimer's disease or of another condition associated with beta amyloid plaque formation and/or beta amyloid peptide neurotoxicity. As used herein, an "animal model of Alzheimer's disease" refers to an animal that exhibits, or that can be induced to exhibit, symptoms or neuropathological features of Alzheimer's disease. Animal models of Alzheimer's disease include transgenic animals that express wild-type or mutant forms of amyloid precursor protein (APP). Optionally, the animal can further exogenously express one or more other genes involved in the APP processing or degradation pathway, such as wild-type or mutant presenilin (PS-1 or PS-2), BACE, insulysin and/or neprilysin, and/or one or more other genes involved in pathogenesis, such as tau. Transgenic animals include, for example, rodents (mice, rats, hamsters, etc.) sheep, goats, chickens, pigs, cattle, monkeys, non-human primates and other non-human vertebrates. The exogenous gene(s) can be expressed in all tissues or only in selected tissues (e.g. neural tissues), at any or all developmental stages, and at physiological, supra- or sub-physiological levels, by appropriate choice of regulatory elements. Transgenic animals can further be homozygous, hemizygous, heterozygous or chimeric for the exogenous gene(s). Transgenic animals can contain the exogenous gene(s) as well as, or instead of (e.g. through "knockin" methodology), the endogenous counterpart. Methods of producing transgenic animals are described in standard laboratory manuals including, for example, Hogan et al., (1994), Manipulating the Mouse Embryo: A Laboratory Manual, 2nd ed., Cold Spring Harbor Laboratory, New York.

APP-expressing transgenic animals are known in the art, and include the Tg2576 mouse, which contains human APP695 with the Swedish (Lys670Asn, Met671Leu) double mutation under the control of the hamster prion protein gene promoter (Hsiao et al. (1996) Science 274:99-102; U.S. Pat. No. 5,877,399); the V717F PDAPP mouse, which contains human APP695 (Val717Phe) under the control of the platelet derived growth factor β (PDGF-β) chain gene promoter (Games et al. (1995) Nature 373:523-527; U.S. Pat. No. 5,811,633); and the C100 mouse, which contains the neurotoxic C-terminal 100 amino acids of APP under the control of the dystrophin neural promoter (Neve et al. (1996) Neurobiol. Aging 17:191-203; U.S. Pat. No. 5,672,805).

Another objective of the present invention is to engineer the insulysin molecule so as to have it either expressed as an extracellular plasma membrane protein or be secreted. Neprilysin will be engineered to be secreted. Such forms of insulysin and neprilysin are introduced into primary hippocampal cells through a viral vector and should make these cells resistant to the neurotoxic effects of Aβ peptides. Previous studies (K. Vekrellis et al. (1999) Soc. For Neurosci Abstracts 25, 302; and K. A. Seta and R. A. Roth (1997) Biochem. Biophys. Res. Commun. 231, 167-171) have shown that a small fraction of insulysin can be expressed on the cell surface and that insulysin can be secreted into the media Neprilysin is normally found on the cell surface. Thus insulysin can be transported to the cell surface and fold properly, however this appears to be an inefficient process as most of the insulysin is found within the cell. Two domains from the β subunit of the peptidase meprin (G. Johnson, G. and L. B. Hersh, L. B. (1992) *J. Biol. Chem.* 267, 13505-13512) are used to place insulysin on the cell surface. The C-terminal region of the rat meprin β subunit has been shown to anchor the protein to the plasma membrane while the N-terminal region of rat meprin β has a secretion signal (G. Johnson, G. and L. B. Hersh, L. B. (1994) *J. Biol. Chem.* 269, 7682-7688). The rat meprin β subunit cDNA was originally cloned in this laboratory and thus we have experience working with both the protein and its cDNA. The cDNA is used as a template for PCR to obtain the C and N-terminal coding sequences and ligate them to the rat insulysin cDNA. The fusion at the C-terminal region is such that the SKL peroxisomal targeting signal found at the C-terminus of insulysin is removed. The construct is assembled initially in pBluescript and then transferred to the adenovirus expression vector system of He et al. (T-C He et al. (1998) *Proc. Natl. Acad. Sci. U.S.A.* 95, 2509-2514) This system permits the generation of a recombinant adenoviral plasmid in *E. coli*, and the use of this plasmid to obtain virus from mammalian cells (i.e. 911E4 cells) without the need for plaque purification. It greatly facilitates the generation of recombinant adenovirus constructs.

To obtain a secreted form of insulysin we either simply leave off the C-terminal domain of the rat meprin β subunit or substitute the C-terminal domain of the rat meprin α subunit for the C-terminal domain of the rat meprin β subunit. We have shown that the C-terminal domain of the rat meprin α subunit, although very similar in sequence to the β subunit, is efficiently cleaved and secreted from cells (G. Johnson, G. and L. B. Hersh, L. B. (1994) *J. Biol. Chem.* 269, 7682-7688).

The virus constructs containing the modified insulysin or neprilysin forms are initially expressed in CHO cells to test targeting to the cell surface or secretion. This is accomplished in two ways. Plasma membrane expression is determined using cell surface biotinylation with biotinamidocaproic acid 3-sulfo-N-hydroxysuccimimide a cell impermeable labeling reagent, which has been shown to label plasma membrane insulysin (K. A. Seta and R. A. Roth (1997) *Biochem. Biophys. Res. Commun.* 231, 167-171). insulysin expressed as an intracellular protein is used as a control. Secondly, we demonstrate that the surface expressed insulysin and neprilysin is enzymatically active by incubating cells expressing insulysin or neprilysin on the surface with β-endorphin, a good insulysin substrate (A. Safavi et al. (1996) *Biochemistry* 35, 14318-14325), and showing that the extracellular, but not the intracellular form of insulysin, can degrade β-endorphin. HPLC is used to follow β-endorphin hydrolysis (A Safavi et al. (1996) *Biochemistry* 35, 14318-14325). We have previously used this protocol to study the degradation of β-endorphin by intact macrophages (B. Sarada, D. Thiele et al. (1997) *J. Leukocyte Biol.* 62, 753-760). Although insulin is the most widely used substrate for the enzyme, the possibility that it would be internalized through insulin receptors and degraded intracellularly precludes its use.

Western blot analysis of conditioned media as well as the measurement of β-endorphin hydrolysis by conditioned media from cells expressing the secreted form of insulysin or neprilysin is used to measure secretion of the enzyme. A control includes is cells expressing intracellular insulysin or membrane associated neprilysin.

Once we demonstrate that insulysin and neprilysin are expressed on the plasma membrane or secreted we express these insulysin forms in primary hippocampal and cortical cells through a viral vector. Intracellularly expressed insulysin is used as a control. The insulysin and neprilysin expressing hippocampal and cortical cells are tested for their sensitivity to the toxic effects of $A\beta_{1-40}$ and $A\beta_{1-42}$ as described above. We compare the concentration dependence and time dependence of $A\beta_{1-40}$ and $A\beta_{1-42}$ induced cell toxicity as described above. We adapt the Aβ deposition assay such that these modified cells are added to the 96 well plates during the assay. We then determine the effectiveness of secreted or cell surface expressed insulysin and neprilysin in preventing Aβ deposition. These experiments permit us to assess the use of insulysin and neprilysin to prevent amyloid fibrils and plaques in vitro.

After analyzing the in vitro data, we express cell surface or secreted insulysin and neprilysin in a transgenic mouse model of Alzheimer's disease. Examples include the R1.40-Homo-G9 Hemi transgenic mouse, or the PDGF-APP$_{Sw, Ind}$ mouse that expresses the human APP protein with the Swedish and Indiana mutations under the control of the platelet-derived growth factor (PDGF) B chain promoter (A. Y. Hsia, E. Masliah, L. McConlogue, G. Q. Yu, G. Tatsuno, K. Hu, D. Kholodenko, R. C. Malenka, R.& Nicoll, L. Mucke L. *Plaque-independent disruption of neural circuits in Alzheimer's disease mouse models*. Proc. Natl. Acad. Sci. 96 (1999) 3228-3233) or other mammalian models of Alzheimer's disease. At ages from 1-6 months we introduce into the right frontal cortex or right hippocampus our adenovirus or lentivirus constructs expressing secreted or cell surface forms of insulysin and neprilysin. Injections are made using a Hamilton syringe with a 33-gauge needle mounted on a Kopf stereotaxic device. Varying amounts of virus are initially tested in order to produce maximal cell infection and expression of the transgene. Mice at 2, 4, and 6 months are sacrificed to test for both the efficiency of infection (i.e. number of cells expressing the insulysin or neprilysin transgene) and the length of continued expression of the transgene using insulysin and meprin immunohistochemistry or neprilysin immunohistochemistry. To increase the expression time of the transgene and decrease cellular immunity we use an adenovirus (Ad5) containing a temperature sensitive DNA binding protein as well as injecting monoclonal Aβs against CD4 and CD45 to immunosuppress the animals (M. I. Romero and G. M. Smith (1998) *Gene Therapy* 5, 1612-1621). This regimen has been shown to effectively increase expression of the transgene as well as permit multiple injections of adenovirus (M. I. Romero and G. M. Smith (1998) *Gene Therapy* 5, 1612-1621). The temperature sensitive adenovirus has been found to express transgenes in mice for 3-4 months (M. I. Romero and G. M. Smith (1998) *Gene Therapy* 5, 1612-1621). Lentivirus can be used directly. An alternative approach is to use a cellular promoter, i.e. the β-actin promoter, in our virus construct since it has been shown that cellular promoters express longer than the standard viral promoters commonly used with virus vectors (G. M. Smith and M. I. Romero (1999) *J. Neurosci. Res.* 55, 147-157).

Once optimal amounts of virus and the number of times it needs to be introduced to maintain cells expressing insulysin on the surface or secreted are determined, we examine the effect of these insulysin and neprilysin forms in preventing fibrillar Aβ deposits in vivo with the R1.40-Homo-G9 Hemi transgenic mouse, or the PDGF-APP$_{Sw, Ind}$ mouse that expresses the human APP protein with the Swedish and Indiana mutations under the control of the platelet-derived growth factor (PDGF) B chain promoter (A. Y. Hsia, B. Masliah, L. McConlogue, G. Q. Yu, G. Tatsmio, L Hu, D. Kholodenko, R. C. Malenka, R. A. Nicoll, L. Mucke L. *Plaque-independent disruption of neural circuits in Alzheimer's disease mouse models*. Proc. Natl. Acad. Sci. 96 (1999) 3228-3233) or other mammalian models of Alzheimer's disease. We stain treated control mice (virus with intracellular form of insulysin) on the injected side and on the contralateral side with thioflavin S and silver using standard histochemical methods (D. R. Borchelt et al. (1997) *Neuron* 19, 939-945). A quantitative estimate of the effectiveness of insulysin and neprilysin in preventing or reducing amyloid deposits is obtained by immunoctyochemical measurement of β-amyloid load as described by Geddes (T. L. Tekirian et al. (1998) *J. Neuropath. Exp. Neurol.* 57, 76-94). It is expected that fewer fibrillar Aβ deposits are seen on the injected side in treated mice compared to control mice.

Next, if the insulysin and neprilysin expressed on the cell surface or secreted can prevent Aβ deposition, we use the same paradigm to see if either of these insulysin and neprilysin forms affect preformed Aβ deposits. In this case the R1.40-Homo-G9 Hemi transgenic mouse, or the PDGF-$APP_{Sw, Ind}$ mouse that expresses the human APP protein with the Swedish and Indiana mutations under the control of the platelet-derived growth factor (PDGF) B chain promoter (A. Y. Hsia, E. Masliah, L. McConlogue, G. Q. Yu, G. Tatsuno, K. Hu, D. Kholodenko, R. C. Malenka, R. A. Nicoll, L. Mucke L. *Plaque-independent disruption of neural circuits in Alzheimer's disease mouse models.* Proc. Natl. Acad. Sci. 96 (1999) 3228-3233) or other mammalian models of Alzheimer's disease are treated with the insulysin and neprilysin virus constructs at time periods of seven to nine months, a time at which the Aβ deposits will have already formed (B. T. Lamb et al. (1999) *Nat. Neurosci.* 2, 695-6697). We compare the treated and contralateral side as well as treated and untreated mice to see if the introduced insulysin and neprilysin has decreased the number of Aβ deposits.

The third objective, expression of amyloid inactivating enzyme vector constructs in neural tissue, has also been shown by introducing neprilysin into hippocampal neurons through a viral vector. Expression of neprilysin via viral constructs made the hippocampal neurons refractory to the neurotoxic effects of Aβ. Viral constructs expressing recombinant human neprilysin were generated and used to infect primary hippocampal neurons. The infected neurons expressed neprilysin activity, and became resistant to the neurotoxic effects of Aβ. We have also injected the viral constructs expressing recombinant human neprilysin into the brains of the PDGF-$APP_{Sw, Ind}$ mice described above, and shown that amyloid plaque formation is greatly inhibited at nine months of age.

Taken together these in vitro and in vivo experiments demonstrate the usefulness of insulysin and neprilysin to protect against both the neurotoxicity of Aβ and to prevent Aβ from being deposited onto amyloid plaques Another preferred embodiment of the present invention involves a pharmacological approach to using insulysin and neprilysin to prevent plaque formation and promote the dissolution of preformed amyloid plaques. The application is also directed to using pharmaceutical agents to treat Alzheimer's patients. We use steroids and analogs thereof to increase endogenous amyloid peptide inactivating enzyme activity. In other words, a pharmaceutical composition comprising at least one steroid or analog thereof (e.g., estrogen, androgens, or their derivatives) is administered to a patient in need thereof to increase endogenous levels of amyloid peptide inactivation enzymes such as neprilysin (NEP) and insulysin (IDE). The pharmaceutical composition is also administered for the treatment of Alzheimer's patients.

In conducting the aims of this preferred embodiment we first determine the ability of an estrogen, androgen, or their derivatives to increase expression of amyloid peptide inactivation enzymes in the brain Second, we determine the activity of amyloid peptide inactivation enzymes in the brain upon administration of an estrogen, androgen, or their derivatives. The third objective is to determine the effects of estrogen androgens, or their derivatives on induced amyloid peptide inactivation enzyme activity and on Aβ peptide levels in the brain. Lastly, we test the effects of estrogen androgens, or their derivatives on induced amyloid peptide inactivation enzyme activity on the inhibition and prevention of amyloid plaque formation and growth in mice expressing various forms of the human amyloid precursor protein. Examples include the R1.40-Homo-G9 Hemi transgenic mouse, or the PDGF-$APP_{Sw, Ind}$ mouse that expresses the human APP protein with the Swedish and Indiana mutations under the control of the platelet-derived growth factor (PDGF) B chain promoter (A. Y. Hsia, B. Masliah, L. McConlogue, G. Q. Yu, G. Tatsuno, K. Hu, D. Kholodenko, R. C. Maleizka, R. A. Nicoll, L. Mucke L. *Plaque-independent disruption of neural circuits in Alzheimer's disease mouse models.* Proc. Natl. Acad. Sci. 96 (1999) 3228-3233) or other mammalian models of Alzheimer's disease.

Although applicants do not wish to be bound by theory, current theory suggests that a decrease in amyloid beta peptide catabolism is in part responsible for the increase in amyloid beta peptide accumulation in the brain of Alzheimer's patients and the subsequent formation of amyloid plaques (see Yasojima, K., Aidyama, H. McGeer, E. G. and McGeer, P. L. *Reduced neprilysin in high plaque areas of Alzheimer brain: a possible relationship to deficient degradation of beta-amyloid peptide*, Neurosci Lett. 297 (2001), 97-100. and Yasojima, K, McGeer, E. G. and McGeer, P. L. *Relationship between beta amyloid peptide generating molecules and neprilysin in Alzheimer disease and normal brain.* Brain Res. 919 (2001), 115-121).

Although it has been established that steroids can increase the transcription of the peripheral forms of neprilysin (Casey, M. L., Smith, J. W., Nagai, K., Hersh, L. B. and MacDonald, P. C. *Progesterone-Regulated Cyclic Modulation of Membrane Metalloendopeptidase (Enkephalinase) in Human Endometrium.* (1991) J. Biol. Chem. 266, 23041-23047, and Shen, R., Sumitomo, M., Dai, J., Hardy, D. O., Arroyo, D., Usmani, B., Papandreou, C. N., Hersh, L. B., Shipp, M. A., Freedman, L. P., and Nanus, D. *Identification and characterization of two androgen response regions in the human neutral endopeptidase gene.* Molecular and Cellular Endocrinology (2000)., 170, 131-142) it has not been established until now that steroids and analogs thereof can increase transcription of neprilysin in the brain. The majority of the brain neprilysin mRNA is derived from a different promoter than the forms of neprilysin mRNA expressed in the periphery, and as a result, it was unexpected that steroids would increase transcription of neprilysin in the brain.

In particular, the neprilysin gene spans more than 80 kb and is composed of 24 exons. Exon 1, 2 and 3 encode 5' untranslated regions (UTRs) of the sequence. Exon 4 is the first coding exon. Each of the three exons 1, 2 and 3 have different promoters resulting in tissue specific transcriptional regulation where the transcription of different mRNAs are subsequently translated into the enzyme and thereby differentially expressed in different tissue types. Transcription of exon 1 leads to the majority of the endogenous neprilysin (NEP) expression in the brain. High levels of exon 2 promoted neprilysin are found in the liver and kidney. Neprilysin promoted by exon 3 is found in both brain and peripheral tissues, but at rather low levels. Exon 4, the first coding region, is found everywhere neprilysin is expressed.

We have made radioactive labeled antisense (AS) and sense (S) probes for each of the exons 1, 2, 3 and 4, and performed in situ hybridization in rat brain. The sense probes (the control), as expected, did not hybridize to the targeted exon. The antisense probes were shown to hybridize in the brain, especially in the regions of the hippocampus including the dentate gyrus and caudate (data not shown).

Once it was established that our antisense probes were capable of hybridizing to neprilysin in the brain, we demonstrated the effects of ovariectomy and estrogen on neprilysin mRNA expression in the hippocampus. Using in situ hybridization we administered antisense probes for each of exons 1, 2, 3, and 4 (R1, R2, R3 and R4, respectively) to the brains of ovariectomized rats, some of which also received estrogen replacement therapy. Adult female Sprague-Dawley rats (approximate weight 300 grams) were used to study the effects of ovariectomy and estradiol supplementation on neprilysin expression levels and activity. In situ hybridization was used to measure neprilysin mRNA levels while a coupled chromogenic assay [Li, C. and Hersh, L. B. *Neprilysin: Assay Methods, Purification and Characterization. Methods in Enzymology.* 248, 253-263 (1995)] was used to measure neprilysin activity. Ovariectomy was performed at 13 weeks of age and sham-surgery was performed on littermate animals to provide a control group. For estrogen replacement groups, ovariectomized animals were implanted with 17β-estradiol pellets (Innovative Research of America, Sarasota, Fla., USA). Rats were killed 3 weeks later after implantation. The brains were rapidly removed, quickly frozen over dry ice, and stored at −80° C. until father processing. At the same time, the plasma was collected for estradiol measurements. The brains were used either for in situ hybridization or for neprilysin activity measurements as noted above.

We have shown from the in situ hybridization analysis that estrogen replacement in ovariectomized rats results in an increase in neprilysin mRNA expression in the brain, especially in the hippocampus. The largest increase was seen in the type 1 neprilysin transcript. Accordingly, we have established that the use of estrogen to increase neprilysin expression represents a new approach toward the treatment of Alzheimer's disease After establishing the increased neprilysin mRNA levels in ovariectomized rats that received estrogen, the second objective of this preferred embodiment is demonstration of neprilysin activity in the brain. Neprilysin activity was determined by measuring the cleavage of the fluorogenic peptide glutaryl-Ala-Aa-Phe-4-methoxy-2-naphthylamide (or similar compounds) as described by Li and Hersh [Li, C. and Hersh, L. B. *Neprilysin: Assay Methods, Purification and Characterization. Methods in Enzymology.* 248, 253-263 (1995). In this assay glutaryl-Ala-Phe-4-methoxy-2-naphthylamide is cleaved to glutaryl-Ala-Ala and Phe-4-methoxy-2-naphthylamide. An aminopetidase is then used to cleave the Phe-4-methoxy-2-naphthylamide releasing fluorescent 4-methoxy-2-naphthylamine which is quantified on a spectrofluorometer. Using this assay we have shown that there is an increase in the activity level of neprilysin in the brains of ovariectomized rats that received estrogen replacement. Accordingly, the increased levels of neprilysin activity in the brain due to estrogen demonstrate the usefulness of estrogen to increase the protective effects of neprilysin against Alzheimer's disease.

After analyzing in vitro data, we demonstrate the third objective of this preferred embodiment, the modulation of Aβ peptide levels by estrogen in vivo according to the method of Zheng et al. (2002). We use adult female Sprague-Dawley rats (approximate weight 300 grams) as described above to study the effects of ovariectomy on endogenous amyloid beta peptide levels in the brain by ELISA. At ages of 13 weeks we perform ovariectomy on the estrogen treated group and sham-surgery on littermate animals to provide a control group. For estrogen replacement groups, ovariectomized animals are implanted with 17β-estradiol pellets (Innovative Research of America, Sarasota, Fla., USA). Rats are killed 3 weeks later after implantation. The brains are rapidly removed, quickly frozen over dry ice, and stored at −80° C. until analyzed. We use a sandwich ELISA to compare the treated and control groups to determine if the introduced estrogen has decreased the level of Aβ peptides in the brain.

Lastly, we demonstrate the ability of estrogen induced NEP activity to prevent formation and growth of Aβ plaques in vivo. In this case we use the PDGF-APP$_{Sw, Ind}$ mouse that expresses the human APP protein with the Swedish and Indiana mutations under the control of the platelet-derived growth factor (PDGF) B chain promoter or a similar mouse model of Alzheimer's disease. We perform ovariectomy on these mice, and then have one group treated with estrogen pellets and the other without. At 3, 6, and 9 months the animals are sacrificed and the amount of amyloid plaque formed determined by histochemical analysis of brain. We compare the estrogen treated and untreated groups to determine if the introduced estrogen has prevented or decreased the number of A plaques in the brain. A further embodiment utilizes the PDGF-APP$_{Sw, Ind}$ mouse crossed with a neprilysin deficient mouse. The effect of estrogen replacement therapy on amyloid plaque formation in the absence of neprilysin is compared to that in its presence to provide additional evidence that at least a part of the action of estrogen on reducing amyloid plaques is through its effect of increasing neprilysin activity.

In a further embodiment, we have found that peptides increase the activity of insulysin. We screen chemical libraries to find stable peptides or peptide analogs that increase insulysin activity and that can be used for the development of lead compounds. Moreover, lead compounds are used for the development of pharmacological agents that can be used for the treatment of Alzheimer's disease by increasing endogenous insulysin activity. A similar screen is used to identify lead compounds that increase neprilysin activity. Identified lead compounds are tested in rats or the Alzheimer's disease transgenic mouse model to determine if they increase brain insulysin activity in vivo and for their ability to prevent amyloid plaque formation in the PDGF-APP$_{Sw, Ind}$ mouse that expresses the human APP protein with the Swedish and Indiana mutations under the control of the platelet-derived growth factor (PDGF) B chain promoter or a similar mouse model of Alzheimer's disease.

Taken together these experiments provide an indication as to insulysin's and neprilysin's use in preventing Aβ deposition in Alzheimer's patients.

Other possibilities include endopeptidase 24.15 (E.C. 3.4.24.15), endopeptidase 24.16 (E.C. 3.4.24.16), endothelin converting enzyme, angiotensin converting enzyme, or similar peptidases.

The following examples are offered by way of illustration of the present invention, and not by way of limitation.

EXAMPLES

Example 1

In order to determine whether the insulysin cleavage of Aβ peptides produces products which in themselves are neurotoxic, we conducted experiments using cultured primary hippocampal cells. In this experiment we preincubated Aβ$_{1-42}$ with insulysin and compared the effect of the insulysin treated Aβ$_{1-42}$ to the intact peptide. An inactivated form of insulysin was used as a control. In a second paradigm we added insulysin directly to hippocampal cell cultures at the same time in which these cells were treated with $A\beta_{1-42}$. In both types of experiments, treatment with insulysin prevented $A\beta_{1-42}$ induced cell death.

Referring to FIG. 1, A represents control hippocampal cells incubated in media for 24 hrs. B is the same as A treated with 10 µM $A\beta_{1-42}$ (initially monomeric). C is the same as A treated with 10 µM $A\beta_{1-42}$ (initially monomeric)+400 ng of insulin degrading enzyme. D is the same as A treated with 10 µM $A\beta_{1-42}$ (initially monomeric)+400 ng of inactive insulin degrading enzyme. Viable cells were detected by microscopy.

Example 2

Non-Neurotoxic Insulysin Breakdown of $A\beta_{1-42}$

It has been previously established that a culture of rat brain hippocampal neurons is a good model for studying the neurotoxicity of amyloid peptides towards neurons in brains of patients with Alzheimer's disease. The addition of amyloid beta peptide ($A\beta_{1-42}$) to the hippocampal cell cultures has been shown to be sufficiently toxic and is thought to accurately reflect the action of $A\beta_{1-42}$ in patients' brains. The object of this experiment was to see if insulysin (insulin degrading enzyme) could break down $A\beta_{1-42}$ into fragments that are no longer neurotoxic. A setup was used where rat brain cells were treated with 25 µM $A\beta_{1-42}$ in the absence and presence of insulysin. The results show that the cells treated with $A\beta_{1-42}$ and insulysin were protected from oxidative damage.

Methods

Rat hippocampal cells were taken in culture dishes and treated with 25 µM $A\beta_{1-42}$ in the presence and absence of insulysin for up to 12 hours. Neuronal survival was estimated as a function of time. Untreated hippocampal cells were relatively unaffected after 12 hours while cells treated with 25 µM $A\beta_{1-42}$ decreased to 20% of the initial number after 12 hours. When insulysin was added with 25 µM $A\beta_{1-42}$ to the cells, survival was close to that seen in the control untreated cells. Heat killed insulysin was used as a control to show that the neuroprotection seen with insulysin required enzymatically active insulysin.

Example 3

Inhibition of Deposition of $A\beta_{1-40}$ Fragments on Amyloid Plaques

A protocol was used where amyloid beta 1-40 ($A\beta_{1-40}$) is initially deposited onto a 96 well microtiter plate. Radioactive ($^{125}I$ labeled) $A\beta_{1-40}$ is then added to the wells of this plate where it further adds to the $A\beta_{1-40}$ deposited. This mimics the deposition of $A\beta_{1-40}$ seen in the brains of Alzheimer patients.

The object of this experiment was to see if insulysin (insulin degrading enzyme) could break down $A\beta_{1-40}$ into fragments that are no longer deposited on the amyloid plaques. This demonstrates that insulysin could prevent the continued formation of amyloid deposits in Alzheimer's disease.

Methods 96 well plates were pre-coated with $A\beta_{1-40}$. In the control, 100 pM of $^{125}I$-$A\beta_{1-40}$ was deposited onto the pre-deposited $A\beta_{1-40}$ plaque for three hours (lane 1). insulysin was added at concentrations of 500 ng, 50 ng and 5 ng to the wells along with $^{125}I$-$A\beta_{1-40}$ for three hours (lanes 2 to 4). 50% inhibition of deposition of $^{125}I$-$A\beta_{1-40}$ was seen with 50 ng of insulysin.

Example 4

Materials. $A\beta_{1-40}$ and $A\beta_{1-42}$ were obtained from Bachem (Torrance, Calif.). Solutions were prepared by dissolving the peptide in dimethylsulfoxide (DMSO) to give a stock concentration of 200 µM. The peptide stock was lyophilized and stored at −80° C. until use. The aggregation state of Aβ peptide stock solutions was checked by electron microscopy (Ray et al. (2000) Brain Res 853:344-351) and found to be predominantly, if not exclusively, monomeric. For the in vitro reactions with insulysin, a final concentration of 25 µM $A\beta_{1-40}$ was obtained after bringing the lyophilized peptide into solution with double distilled water. For cytotoxicity studies $A\beta_{1-40}$ and $A\beta_{1-42}$ peptides were dissolved in sterile N2 medium (Life Technologies, Rockville, Md.). Human β-endorphin$_{1-31}$, obtained from the National Institute on Drug Abuse drug supply system, was dissolved in water to give a stock solution of 300 µM. Trifluoroacetic acid (Sigma Biochemicals, St. Louis, Mo.) was diluted into water to produce a 5% working solution.

Example 5

Expression and Purification of Recombinant Insulysin

A rat insulysin cDNA, (pECE-insulysin) was subcloned into the baculovirus derived vector pFASTBAC (GIBCO BRL, Rockville, Md.) through BamH I and Xho I restriction sites such that a $His_6$-affinity tag was attached to the N-terminus of the protein. Generation of recombinant virus and expression of the recombinant protein in Sf9 cells was carried out according to the manufacturer's directions. For the purification of recombinant insulysin, a 1/10 (wt/vol.) suspension derived from a 50 ml culture of viral infected Sf9 cells was prepared in 100 mM potassium phosphate buffer, pH 7.2, containing 1 mM dithiothreitol (K-$PO_4$/DTE buffer). The suspension was sonicated 10 times, each burst for one second, using a Branson sonifier (setting 3 at 30%) and then centrifuged at 75,000 g for 30 minutes to pellet cell debris and membranes. The supernatant containing recombinant rat insulysin was loaded onto a 0.5-ml nickel-NTA column (Qiagen, Valencia, Calif.) that had been equilibrated with the K-$PO_4$/DTE buffer. After extensive washing of the column with starting buffer, and then with 20 mM Imidazole-HCl, pH 7.2, the enzyme was eluted with 0.1 M Inidazole-HCl, pH 7.2. The enzyme was further purified over a 1 ml Mono-Q anion exchange column (Pharmacia Biotech, Piscataway, N.J.) in 20 mM phosphate buffer pH 7.2. A linear salt gradient of 0 to 0.6 M KCl, equivalent to 60 column volumes, was applied to the column with the enzyme eluted at 0.28 M KCl. SDS-PAGE of the insulysin was conducted on a 7.5% gel.

Example 6

Insulysin Activity Determination

Insulysin activity was assayed by measuring the disappearance of β-endorphin by isocratic reverse phase HPLC (Safavi et al. (1996) Biochemistry 1996 35:14318-14325). A 100 µl reaction mixture containing 40 mM potassium phosphate buffer, pH 7.2, 30 µM β-endorphin, and enzyme was incubated for 15 minutes at 37° C. The reaction was stopped by the addition of 10 µl of 5% trifluoroacetic acid to give a final concentration of 0.5%. The reaction mix was loaded onto a $C_4$ reverse phase-HPLC column (Vydac, Hisperia, Calif.) and products resolved isocratically at 32% acetonitrile. The β-endorphin peak was detected by absorbance at 214 nm using a Waters 484 detector. The reaction was quantitated by measuring the decrease in the β-endorphin peak area.

Example 7

Determination of Sites of Cleavage of Aβ Peptides

Purified insulysin was incubated with 25 μM $A\beta_{1-40}$ in 40 mM potassium phosphate buffer, pH 7.2, at 37° C. for 1 hour. The reaction products were loaded onto a $C_4$ reverse phase HPLC column and products resolved using a linear gradient of 5 to 75% acetonitrile over 65 minutes. Products were detected by absorbance at 214 nm using a Waters 484 detector and individual product peaks were collected manually. Product analysis was also conducted on an intact reaction mixture in which products were not resolved by HPLC. Products were identified by matrix assisted laser desorption ionization time of flight mass spectrometry (MALDI-TOF-MS). The reaction of insulysin with $A\beta_{1-42}$ was conducted in a similar manner with products identified by MALDI-TOF-MS directly from reaction mixtures.

Example 8

$A\beta_{1-40}$ Deposition Assay

Beta amyloid deposition assays were conducted as described by Esler et. al. (Esler et al. (1997) *Nat Biotech* 15:268-263). Briefly, 96 well microtiter plates pre-coated with aggregated amyloid $\beta_{1-40}$ (QCB/Biosource, Hopkinton, Mass.) were additionally coated with 200 μl of a 0.1% bovine serum albumin solution in 50 mM Tris-HCl, pH 7.5 for 20 minutes to prevent non-specific binding. For measuring $A\beta_{1-40}$ deposition in the presence or absence of insulysin, a 150 μl solution of 0.1 nM 125I labeled $A\beta_{1-40}$ in 50 mM Tris-HCl, pH 7.5 was added to the pre-coated well and incubated for four hours. When added, insulysin (0.5 to 500 ng) was placed directly in the well at zero time. The reaction was stopped by washing off excess undeposited radiolabeled $A\beta_{1-40}$ with 50 mM Tris-HCl, pH 7.5. The radiolabel deposited onto the washed well was counted in a gamma counter. In a variation of this protocol, insulysin was preincubated with $^{125}$I-$A\beta_{1-40}$ for 60 minutes and then added to the deposition assay.

Example 9

Neuoroprotection Assays

Neurotoxicity assays were performed as described by Estus et. al. (Estus et al. (1997) *J Neurosci* 17:7736-7745) using embryonic day 18 rat fetuses to establish primary rat cortical neuron cultures. Rat brain cortical cells were initially cultured in $AM_0$ media for 3-5 hrs in 16 well chamber slides (Nalge Nunc International, Rochester, N.Y.) pre-coated with polyethyleneimine at a density of ~1×10$^5$ cells per well. The culture was enriched in neurons by replacement of the $AM_0$ media with Dulbecco's modified Eagle's medium (DMEM, Life Technologies, Rockville, Md.) containing 100 units/ml penicillin, 100 μg/ml streptomycin and 2% B27 serum supplement (Life Technologies, Rockville, Md.).

Cells were treated with Aβ peptides and then fixed with 4% paraformaldehyde for 15 min. at room temperature. After washing the cells with PBS they were then stained with Hoechst 33258 at 1 μg/ml for 10 minutes. Neurons were then visualized by fluorescence microscopy. Those cells with uniformly dispersed chromatin were scored as survivors, while those cells containing condensed chromatin were scored as non-survivors. Readings were typically taken in triplicate with a minimum of 250 neurons scored from each well. Cells treated as described above were visualized using a Nikon microscope equipped with a Hoffman modulation contrast lens. Statistical analysis was performed on the samples using ANOVA.

Example 10

Immunofluorescence

The presence of aggregated $A\beta_{1-40}$ was detected in the neuronal cultures using the monoclonal antibody 10D5 (Walker et al. (1994) *J Neuropathol Exp Neurol* 53:377-383) at a 1:100 dilution in 5% goat serum in PBS. After an overnight incubation at 4° C. with this primary antibody, the wells were rinsed with PBS and incubated with a goat anti mouse secondary antibody conjugated to Cy-3 (Jackson ImmunoResearch, West Grove, Pa.) at a dilution of 1:250 in 5% goat serum in PBS. The wells were incubated at room temperature for 60 minutes and then after further washing with PBS, cells were examined under a fluorescence microscope.

Example 11

Results

Figure 4:
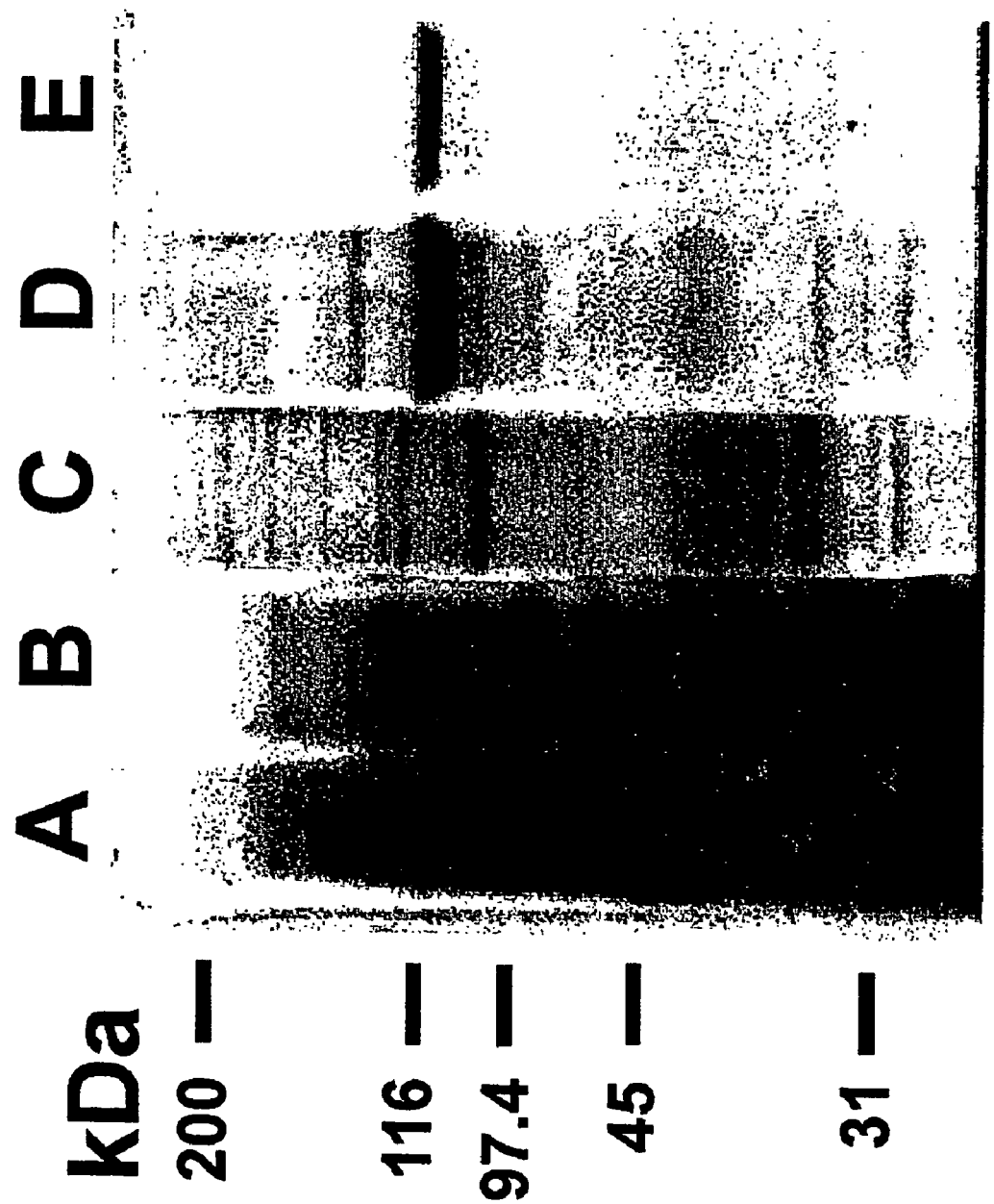
FIG. 4 shows the purification of recombinant rat insulysin, wherein insulysin was purified as described in Examples 4-6 herein and 15 μg aliquots from various stages of purification were analyzed by SDS-PAGE on a 7.5% gel stained with Coomassie Blue. Lane A is Sf9 cell extract. Lane B shows non-bound proteins from the Ni-NTA-agarose column. Lane C shows protein eluted from the Ni-NTA-agarose column with 20 mM imidazole. Lane D shows protein eluted from the Ni-NTA-agarose column with 100 mM imidazole. Lane B shows protein eluted from the Mono-Q column. The position of molecular weight markers (myosin=200 kDa, β-galactosidase=116 kDa, phosphorylase b=97.4 kDa, bovine serum albumin=66 kDa, and ovalbumin=45 kDa) is shown on the left.

To characterize the reaction of insulysin with the Aβ peptides, recombinant rat enzyme containing an amino-terminal $His_6$ affinity tag was expressed in baculovirus infected Sf9 cells. Expression of the enzyme in this system was high as evidenced by the ability to see insulysin protein in a crude extract by SDS-PAGE, FIG. 4. Purification of the recombinant enzyme was achieved by chromatography on a Ni-NTA-agarose column producing highly purified enzyme followed by chromatography on a Mono-Q column, which produced homogeneous enzyme, FIG. 4. The specific activity of the recombinant enzyme (2.6 μmols/min/mg) was comparable to enzyme purified from a thymoma cell line, EL-4 (3.3 μmols/min/mg), and thus the presence of the $His_6$ affinity tag had no discernable effect on enzyme activity.

To delineate the sites of cleavage of the $A\beta_{1-40}$ peptide by insulysin, the peptide was incubated with varying concentrations of the enzyme for one hour at 37° C., and then products were resolved by gradient reverse-phase HPLC. With 50 ng of insulysin, the lowest enzyme concentration used, three major cleavage sites at $His^{14}$-$Gln^{15}$ (peak 1), $His^{13}$-$His^{14}$ (peak 2), and $Phe^{19}$-$Phe^{20}$ (peak 4 and peak 7) were discernable, TABLE, 1 and FIG. 5. In addition, minor cleavage sites at $Lys^{28}$-$Gly^{29}$ (peak 5) and $Phe^{20}$-$Ala^{21}$ (peak 6) was observed. When the amount of insulysin was increased to 250 ng, each of the products seen with 50 ng of enzyme increased, and an additional product corresponding to cleavage at $Val^{18}$-$Phe^{19}$ (peak 3) was observed. Further increasing insulysin to 500 ng showed a continued increase in each of the products. The same products were seen when $A\beta_{1-40}$ was treated with 500 ng of insulysin and analyzed by MALDI-TOF-MS without separation of the reaction products. It is interesting to note that one product peak $A\beta_{14-40}$ was not observed, while other product peaks were not apparent until after substantial metabolism had occurred. For example, $A\beta_{1-14}$ can be seen in the digest using 50 ng of insulysin while the product corresponding to the C-terminal half of this cleavage, $A\beta_{15-40}$, is not seen in the 50 ng reaction, but is observed with the 250 ng of enzyme. This is in part attributed to the hydrophobic nature of the C-terminal peptides and their greater retention times which produces HPLC peak broadening and decreased sensitivity. The overall cleavage profile is illustrated in FIG. 6.

Figure 5:
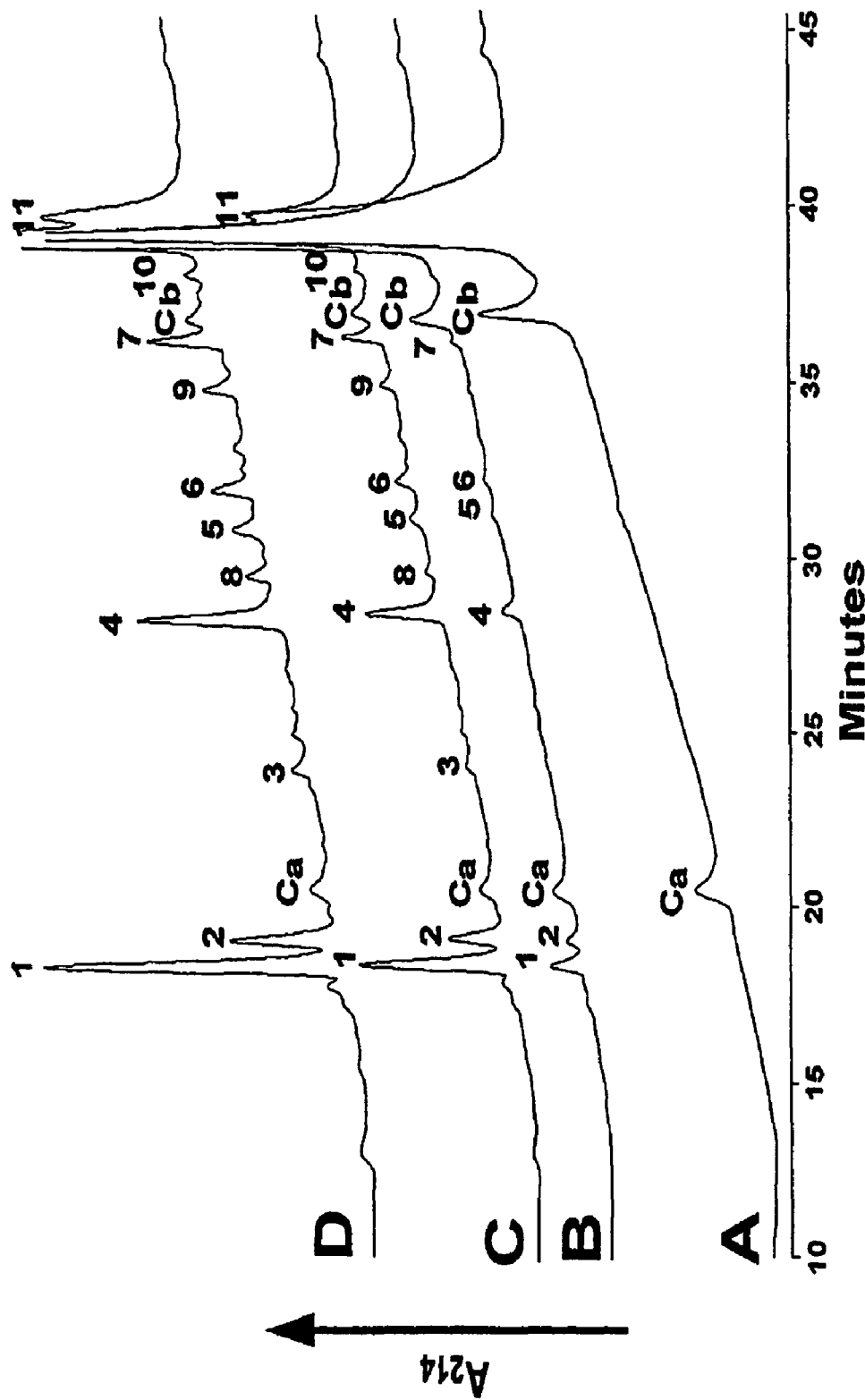
FIG. 5 shows an HPLC profile of products generated from the cleavage of $A\beta_{1-40}$ by insulysin. Varying amounts of recombinant rat insulysin was incubated with 25 μM $A\beta_{1-40}$ for 30 minutes at 37° C. Cleavage products were separated by a 5 to 75% gradient of acetonitrile on a $C_4$ reverse phase HPLC column. Product peaks are numbered according to their order of elution. The peaks designated Ca and Cb refer to contaminants in the $A\beta_{1-40}$ solution. These are not reacted upon by insulysin as is seen by their invariant peak areas in all the traces. Trace A shows $A\beta_{1-40}$ alone. Trace B shows $A\beta_{1-40}$ incubated with 50 ng insulysin. Trace C shows $A\beta_{1-40}$ incubated with 250 ng insulysin. Trace D shows $A\beta_{1-40}$ incubated with 500 ng insulysin. The HPLC scans are skewed 2 min. to the left to permit overlapping peaks to be viewed. The time scale refers to trace A.

The peaks from the HPLC chromatogram shown in FIG. 5 were collected and analyzed by MALDI-TOF. Product peaks are labeled sequentially in TABLE 1 as derived from HPLC (shown in FIG. 5).

TABLE 1

Identification of products from insulysin cleavage of $A\beta_{1\text{-}40}$

| Peak no. | $A\beta_{1\text{-}40}$ Fragment | Sequence |
|---|---|---|
| 1 | 1-14 | DAEFRHDSGYEVHH (SEQ ID NO:1) |
| 2 | 1-13 | DAEFRHDSGYEVH (SEQ ID NO:2) |
| 3 | 1-18 | DARFRHDSGYEVHHQKLV (SEQ ID NO:3) |
| 4 | 1-19 | DAEFRHDSGYEVHHQKLVF (SEQ ID NO:4) |
| 5 | 1-28 | DAEFRHDSGYEVHHQKLVFFAEDVGSNK (SEQ ID NO:5) |
| 6 | 1-20 | DAEFRHDSGYEVHHQKLVFF (SEQ ID NO:6) |
| 7 | 20-40 | FAEDVGSNKGAIIGLMVGGVV (SEQ ID NO:7) |
| 8 | 29-40 | GAIIGLMVGGVV (SEQ ID NO:8) |
| 9 | 21-40 | AEDVGSNKGAIIGLMVGGVV (SEQ ID NO:9) |
| 10 | 19-40 | FFAEDVGSNKGAIIGLMVGGVV (SEQ ID NO:10) |
| 11 | 15-40 | QKLVFFAEDVGSNKGAIIGLMVGGVV (SEQ ID NO:11) |

The $A\beta_{1\text{-}42}$ peptide was incubated with insulysin in an identical fashion as with $A\beta_{1\text{-}40}$ and the products were analyzed by MALDI-TOF mass spectrometry without prior separation by HPLC. Product peaks corresponding to cleavage at the $His^{13}$-$His^{14}$, $His^{14}$-$Gln^{15}$, $Phe^{19}$-$Phe^{20}$ and $Phe^{20}$-$Ala^{21}$ positions were observed. These results indicate that both $A\beta_{1\text{-}40}$ and $A\beta_{1\text{-}42}$ are cleaved at the same sites. The rate of cleavage of 25 µM $A\beta_{1\text{-}40}$ was measured as 1.2 µmols/min/mg enzyme which indicates that the Aβ peptides are good substrates for insulysin.

The products of the action of insulysin on the Aβ peptides produces relatively large fragments. Since the peptide $A\beta_{25\text{-}35}$, which is derived from $A\beta_{1\text{-}40}$, is neurotoxic, it is possible that the products of insulysin action on the Aβ peptides could be toxic to neurons. To test this, rat cortical neurons were treated with Aβ peptides in the presence and absence of insulysin. Preliminary experiments were performed to obtain a suitable Aβ peptide concentration that would show a significant cytotoxic effect, as there are batch to batch variations in the ability of the Aβ peptides to mediate cytotoxic effects on cells in culture. These experiments established 30 µM $A\beta_{1\text{-}40}$ and 25 µM $A\beta_{1\text{-}42}$ as reasonable peptide concentrations which produce approximately 70% and 80% loss of cortical neurons respectively in 48 hrs.

Figure 7:
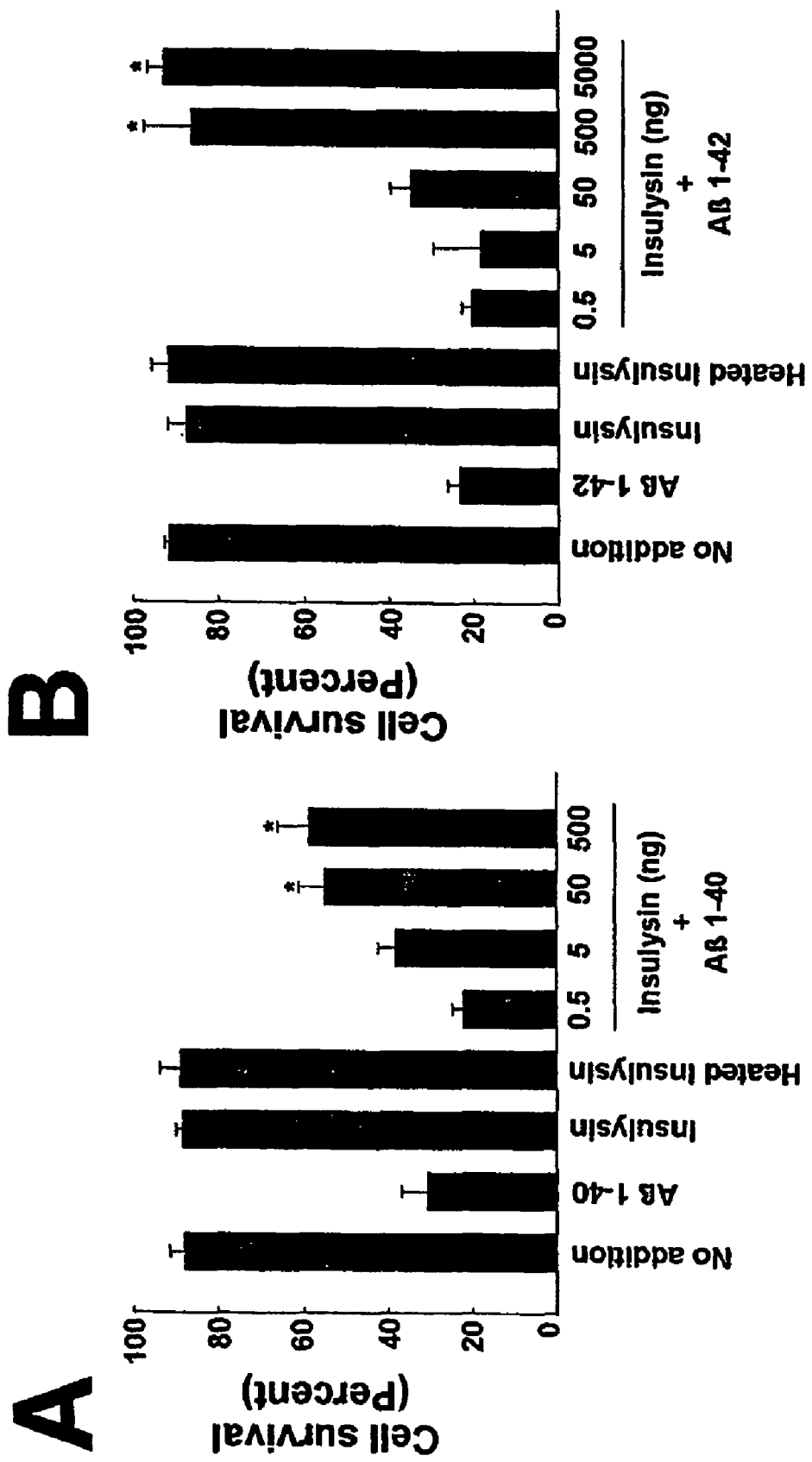
FIGS. 7A and 7B show the effect of insulysin on the neurotoxic effects of Aβ peptides. Purified insulysin was added with $A\beta_{1-40}$ (30 μM) or $A\beta_{1-42}$ (25 μM) to primary cortical neurons, and incubation continued for an additional 48 hrs. The neurotoxic effect of the Aβ peptides was determined as described in Example 9 herein. The insulysin and heat inactivated insulysin controls utilized 5000 ng of enzyme.
Figure 8:
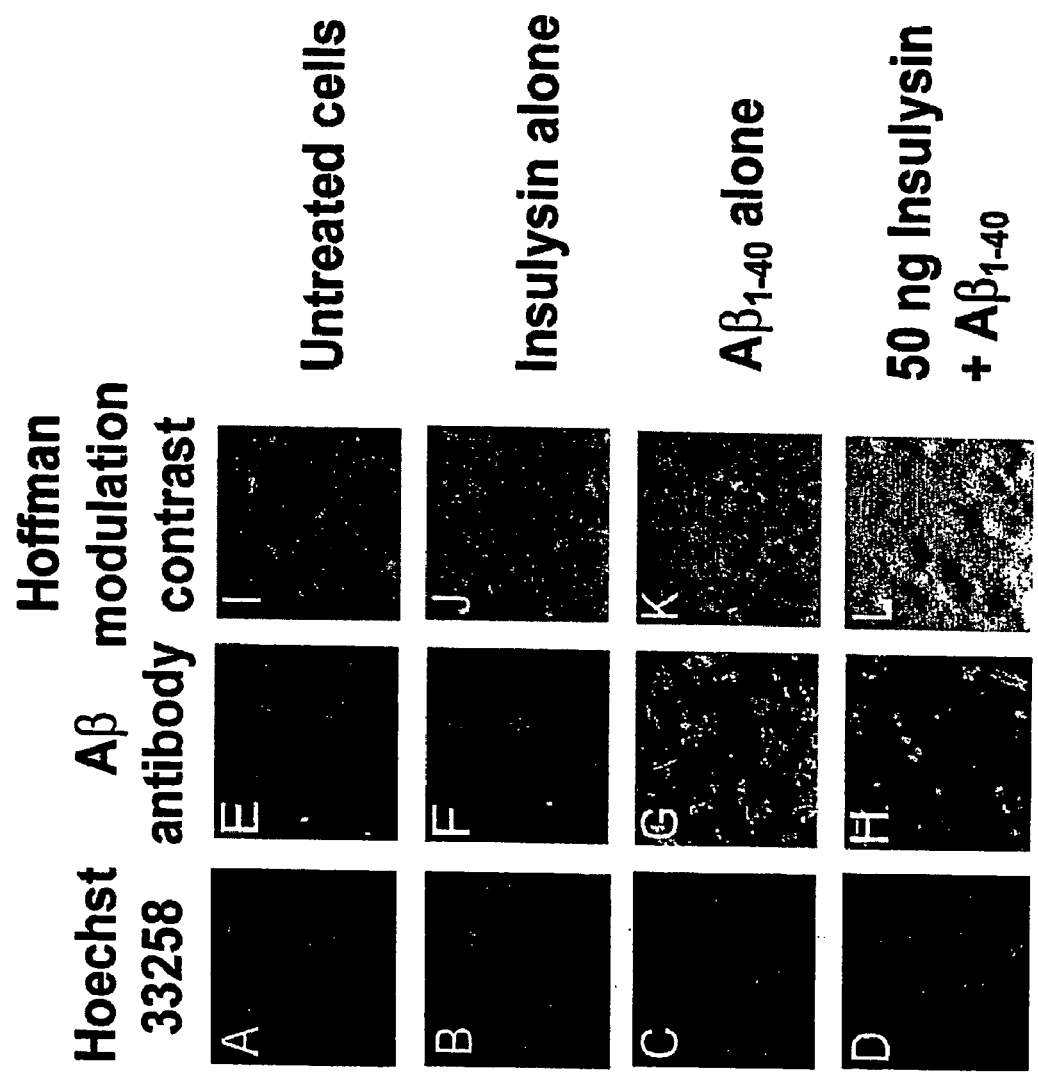
FIG. 8 shows that insulysin protects against $A\beta_{1-40}$ mediated neurotoxicity. Rat cortical neurons were treated as described in FIG. 7 in the presence or absence of 50 ng insulysin. Cells were stained with Hoechst 33258 (panels A-D) or with the Aβ antibody 10D5 (panels E-H). Hoffman modulation contrast micrographs are shown in panels I-L. Panels A, E, and I show untreated neurons. Panels B, F and J show neurons with 50 ng insulysin added. Panels C, G and K show neurons treated with 30 W $A\beta_{1-40}$. Panels D, H and L show neurons treated with 50 ng insulysin and 30 μM $A\beta_{1-40}$.

The cell based assay using primary rat cortical neurons was used to determine whether the insulysin cleavage products of the Aβ peptides were themselves neurotoxic. Recombinant insulysin at concentrations ranging from 0.5 to 5000 ng was added simultaneously with the Aβ peptides to the cortical cultures. When added directly to the cultures as little as 50 ng of insulysin was effective in sparing the neurotoxic effects of $A\beta_{1\text{-}40}$ (FIG. 7A) while 500 ng of insulysin was effective in sparing the neurotoxic effects of $A\beta_{1\text{-}42}$ FIG. 7B). This effect of insulysin is illustrated in FIG. 8 where cells were either stained with Hoechst 33258 to visualize DNA (panels A-D), with the Aβ antibody 10D5 to visualize cell associated Aβ (panels B-H), or visualized directly by Hoffman modulation microscopy (panels I-L). Using this phase contrast microscopy it can be seen that $A\beta_{1\text{-}40}$ caused the cells to appear shrunken (panel K) as compared to control cells which appear rounded (panel 1). $A\beta_{1\text{-}40}$ induced chromatin condensation, which appears as small rounded nuclei (panel C), and Aβ cellular accumulation, which appears as a bright layering over the cells (panel G), is not evident in untreated cells (panels A & B). Cells to which insulysin was added along with $A\beta_{1\text{-}40}$ more closely resembled untreated cells (panels D, H and L). Also shown in FIG. 8 are controls in which cells were treated with insulysin alone (panels B, F and J).

Figure 9:
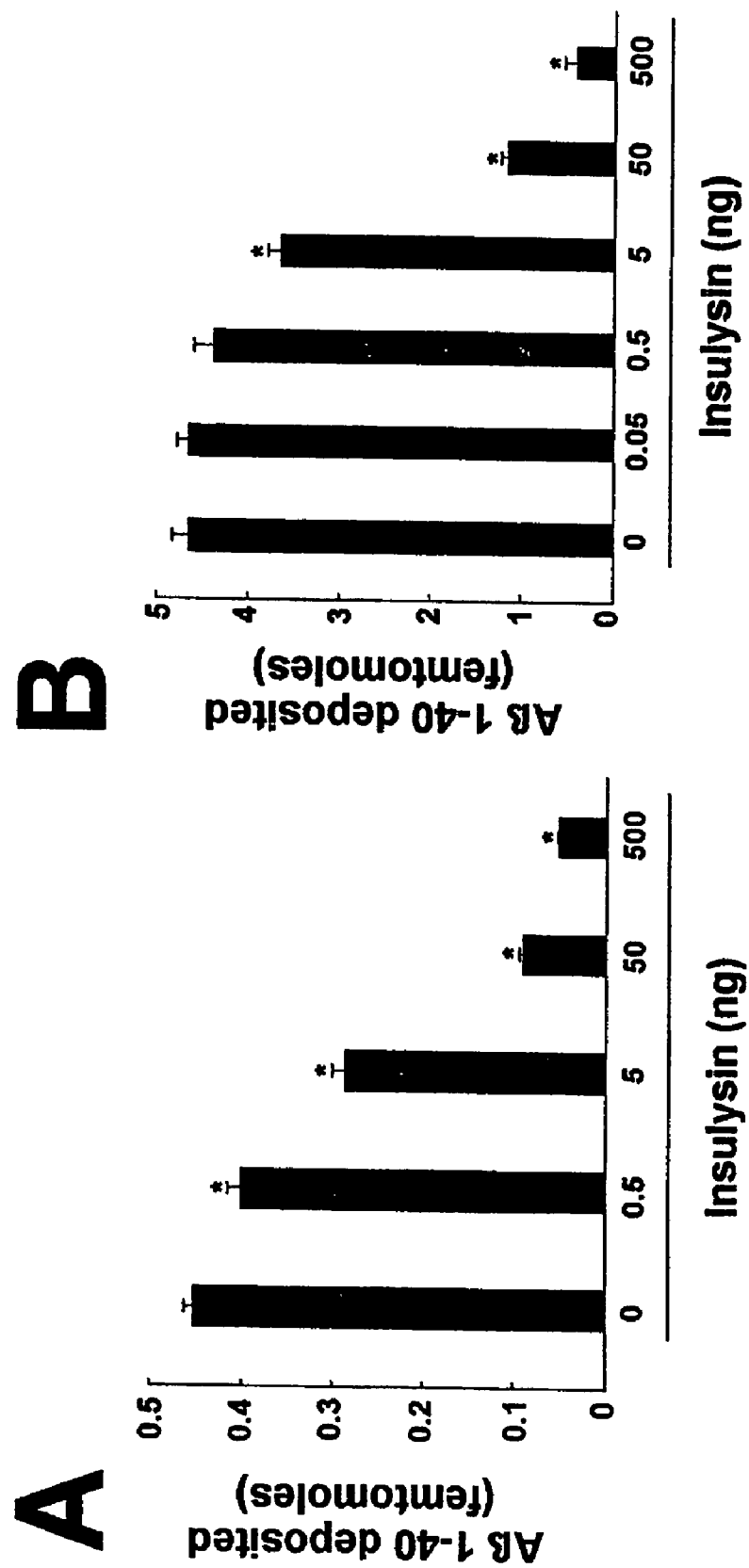
FIGS. 9A and 9B show that insulysin inhibits the deposition of $A\beta_{1-40}$ onto synthetic amyloid plaques.

During the progression of Alzheimer's disease monomeric Aβ peptides are deposited onto senile plaques. To test whether insulysin is able to prevent the deposition of the $A\beta_{1\text{-}40}$ peptide, a model system was used in which the deposition of radiolabeled $A\beta_{1\text{-}40}$ onto a synthetic amyloid plaque (synthaloid) is followed (Esler et al. (1999) *Methods Enzymol* 309:350-74). As seen in FIG. 9A, addition of insulysin at 0.5 ng to 500 ng with radiolabeled $^{125}$I-$A\beta_{1\text{-}40}$ shows that 50 ng of insulysin is able to prevent the deposition of radiolabeled $A\beta_{1\text{-}40}$. FIG. 9B shows that preincubation of insulysin with radiolabeled $^{125}$I-$A\beta_{1\text{-}40}$ for 60 minutes before adding it to the wells also shows that 50 ng insulysin is able to prevent the deposition of radiolabeled $A\beta_{1\text{-}40}$ onto the synthetic amyloid. We also conducted an experiment in which $^{125}$I-$A\beta_{1\text{-}40}$ was first deposited onto the synthetic amyloid and then treated with insulysin to see if the enzyme could degrade pre-aggregated $A\beta_{1\text{-}40}$. After a 24 hr incubation with 5 µg of insulysin no radioactivity was released indicating that insulysin does not degrade aggregated Aβ peptides.

Example 12

Neprilysin Virus Vector Treatment on Aβ Induced Neurotoxicity

Figure 10:
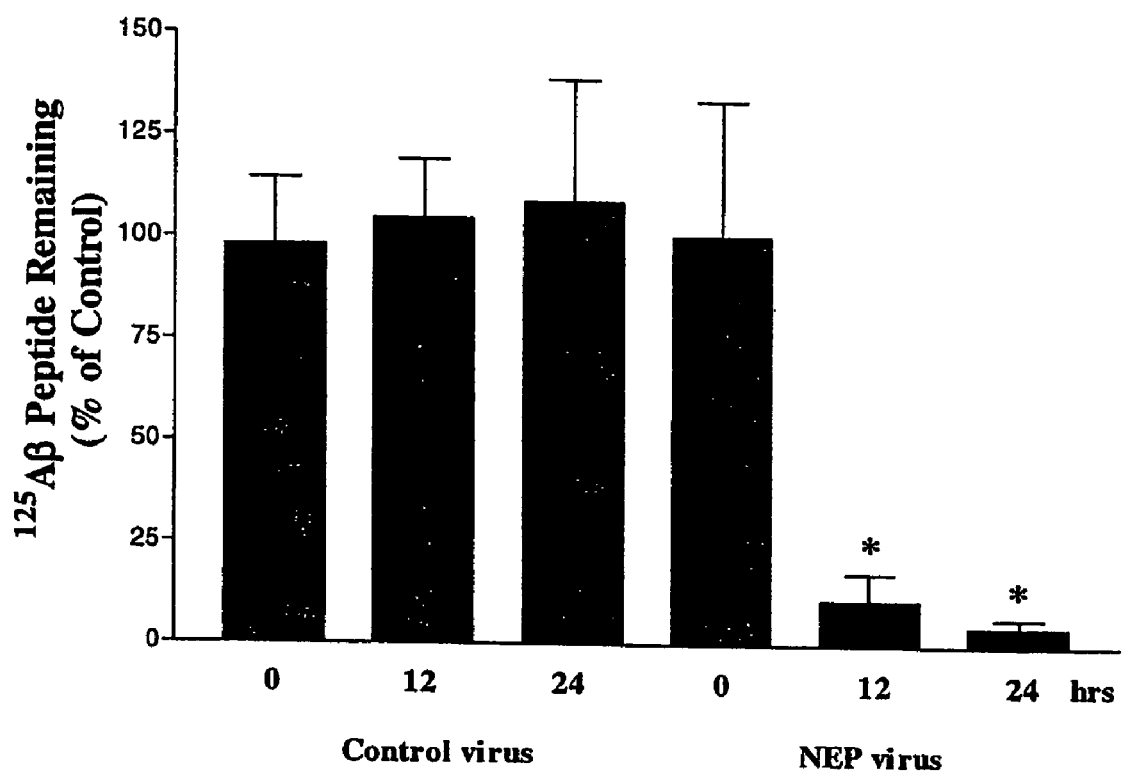
FIG. 10 shows a graphic representation of $125 A\beta_{1-40}$ peptide degradation in primary neuronal cultures from neprilysin deficient mice infected with control virus or virus expressing the human neprilysin s. gene. N=8 cultures for each point.

The full-length human neprilysin cDNA was used in preparation of a lentiviral construct. Primary neuronal cell cultures were established from neprilysin deficient mice ($NEP^{-/-}$). The lentivirus construct was used to express neprilysin in the primary neuronal cell cultures. Shown in FIG. 10 is a graphic presentation of $^{125}A\beta_{1\text{-}40}$ peptide degradation in primary neuronal cultures from NEP deficient mice infected with control virus (control virus) or the human neprilysin virus (NEP virus). N=8 cultures for each point. *, P<0.001 compared to 0, 12 24 hour control and 0 hour NEP cultures and examined for enzyme expression of neprilysin. Primary neuronal cell cultures from wildtype ($NEP^{+/+}$) and neprilysin deficient mice ($NEP^{-/-}$) were subjected to Aβ induced neurotoxicity. Aβ was added to the cultures at 10 µM in a non-fibrillar state. After 48 hrs cultures were examined for the number of dead or dying neurons. *, P<0.01 compared to $NEP^{+/+}$, -Aβ; **, P<0.001 compared to NEP; -Aβ.

Referring to FIG. 10, neprilysin expressing neuronal cell cultures virtually destroyed all Aβ peptide in comparison to the controls.

Example 13

Neprilysin Virus Vector Treatment on Neuronal Cell Survival

The full-length human neprilysin cDNA was used in preparation of a lentiviral construct. Primary neuronal cell cultures were established from neprilysin deficient mice (NEP$^{-/-}$). The lentivirus construct was used to express neprilysin in the primary neuronal cell cultures. Neuronal cell cultures were subjected to Aβ induced neurotoxicity. Aβ was added to the cultures at 10 μM in a non-fibrillar state. After 48 hrs cultures were examined for the number of dead or dying neurons. *, P<0.01 compared to NEP$^{+/+}$, -Aβ; **, P<0.001 compared to NEP$^{-/-}$, -Aβ. Control neuronal cells (CONT) are primary neuronal cells derived from the neprilysin deficient mice, and exhibit sensitivity to Aβ induced neurotoxicity. Control vector neuronal cells (+CONT vector) are primary neuronal cells derived from the neprilysin deficient mice treated with the lentivirus vector, and exhibit sensitivity to Aβ induced neurotoxicity. neuronal cells (+CONT vector) are primary neuronal cells derived from the neprilysin deficient mice treated with the lentivirus vector to express neprilysin (vector+NEP) are much less sensitivity to Aβ induced neurotoxicity, which cells expressing a control protein (GFP) (+GFP vector) retain sensitivity to Aβ induced neurotoxicity.

Figure 11:
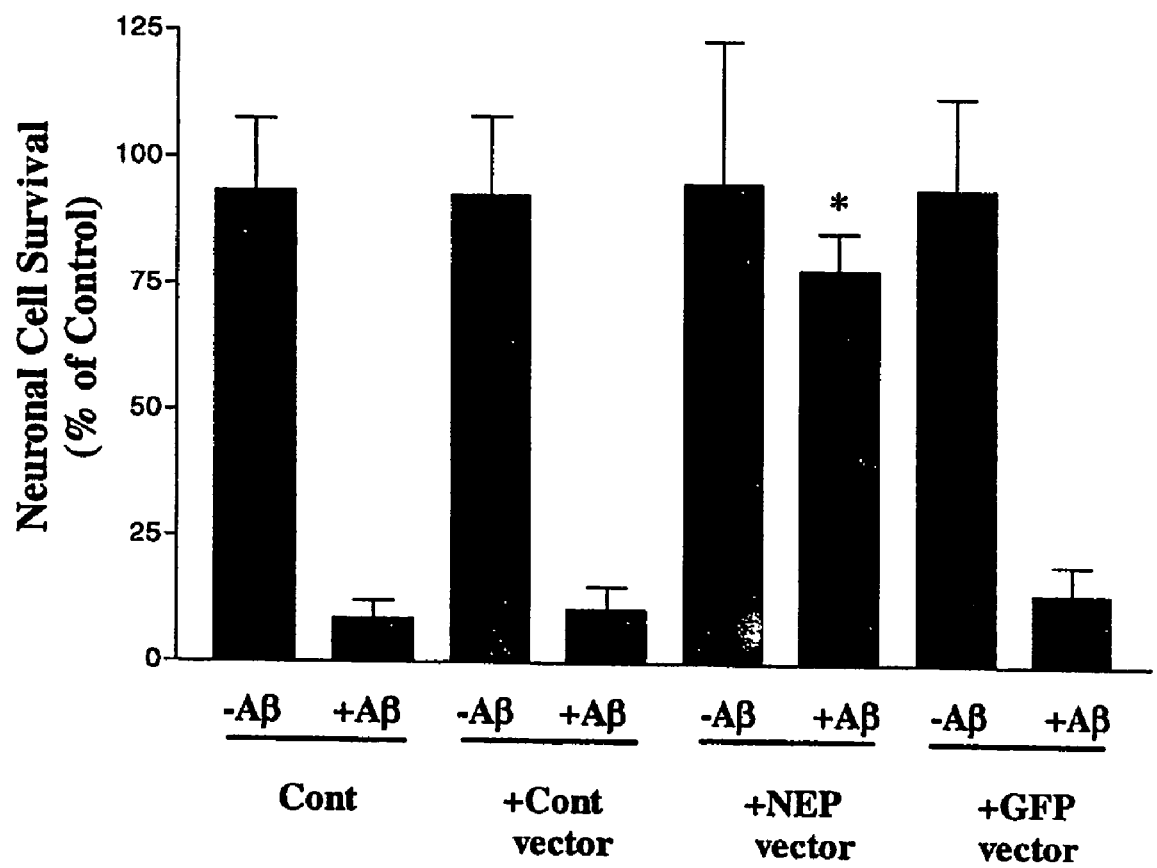
FIG. 11 shows a graphic representation of neuronal cell survival after treatment with Aβ peptide and neprilysin virus.

Referring to FIG. 11, neprilysin treated Aβ induced neurotoxic neuronal cells resulted in about a 75% increase in cell survival of Aβ induced cells.

Example 14

In Vivo Inhibition of Aβ Peptide Plaques

The expression of the human amyloid precursor protein leads to β-amyloid secretion and plaque formation. The mouse of FIG. 12 A received an injection into its hippocampus of a viral construct encoding a control protein (green fluorescent protein). The encircled dark areas of the hippocampus are numerous amyloid plaques that formed. FIG. 12 B is a brain section showing the hippocampus of a same aged mouse that received by injection a viral construct that produces neprilysin. There are very few amyloid plaques formed, and those that appear are light and diffuse areas, considered "immature plaques."

Example 15 mRNA of Neprilysin in the Hippocampus with Estrogen Replacement

In order to determine the expression of neprilysin in the brain, we prepared antisense (AS) and sense (S) cRNA probes for rat neprilysin mRNA forms and performed in situ hybridization. Both antisense (AS) and (S) probes R1, R2, R3 and R4 were made from genomic DNA clones by the polymerase chain reaction (PCR) methods known by one skilled in the art for exons 1, 2, 3 and 4, respectively. The sense probes did not hybridize to neprilysin in the brain sections of rats; the antisense probes did hybridize to neprilysin in the brain sections (data not shown). Tissues were cut into 10 μM thickness sections using a freezing microtome (Microtome Cryostat HM 5000M, MICROM International GmbH). Sections were thaw-mounted onto superfrost plus (VWR) glass slides and stored at −20° C. until farther processing. Slides from all animals were postfixed in 4% paraformaldehyde/0.1M PBS (pH 7.4), acetylated in fresh 0.25% acetic anhydride in 0.1M triethanolamine (pH 8.0), dehydrated in an ascending series of alcohols, delipidated in chloroform and rehydrated in 95% alcohol, air dried and then hybridized. Hybridization was accomplished at 60° C. for 18-24 hours in a solution containing 50% formamide, 10% dextran sulfate, 20 mM Tris-HCl, 1 mM EDTA, 1×Denhardt's solution, 40 mM dithiothreitol, 0.33 mg/ml denatured salmon sperm DNA, 0.15 mg/mL yeast tRNA and the $^{33}$P-labeled cRNA probe. Fifty μL of hybridization buffer with probe were applied to each slide containing four sections and covered with a glass cover slip. Slides were washed two times in 4× standard saline citrate (SSC), treated with ribonuclease inhibitor and washed in descending concentrations of SSC buffer. The slides were then rinsed quickly in deionized water and air-dried. The slides and a set of [$^{14}$C] micro-scale standards on glass slides (American Radiolabeled Chemicals Inc, 0.07-2.15 nCi/mg wet tissue equivalent) were then apposed to film (ICN β-RayMax Hyperfilm) for 9-12 days respectively. The autoradiographic films were developed using the Kodak D-19 developer and Kodak rapid fixer.

Images on autoradiographic film were analyzed with computer-aided densitometry (MCID-M1, Imaging Research, St. Catharines, Ontario, Canada). Optical density values of the [$^{14}$C] microscales were obtained and a correlating log-log linear least-squares fit was calculated ($r^2$>0.99). This standard calibration was used to convert the relative optical densities of the autoradiograms into nCi/mg wet tissue equivalent. The optical density of each defined region was determined for the neuronal somal layer of area CA1 (stratum pyramidale), CA3 and dentate gyrus (stratum granulosum). Identification of brain regions was determined using the atlas of Paxinos and Watson (G. Paxinos, C. Watson, The rat Brain in Stereotaxic Coordinates, second Edition, Academic Press, Australia, 1986). The brain sections came from either of two sources: (1) ovariectomized rats that did not receive estrogen replacement therapy or (2) ovariectomized rats that received estrogen replacement therapy by implanting 17β-estradiol pellets (Innovative Research of America, Sarasota, Fla., USA).

Figure 13:
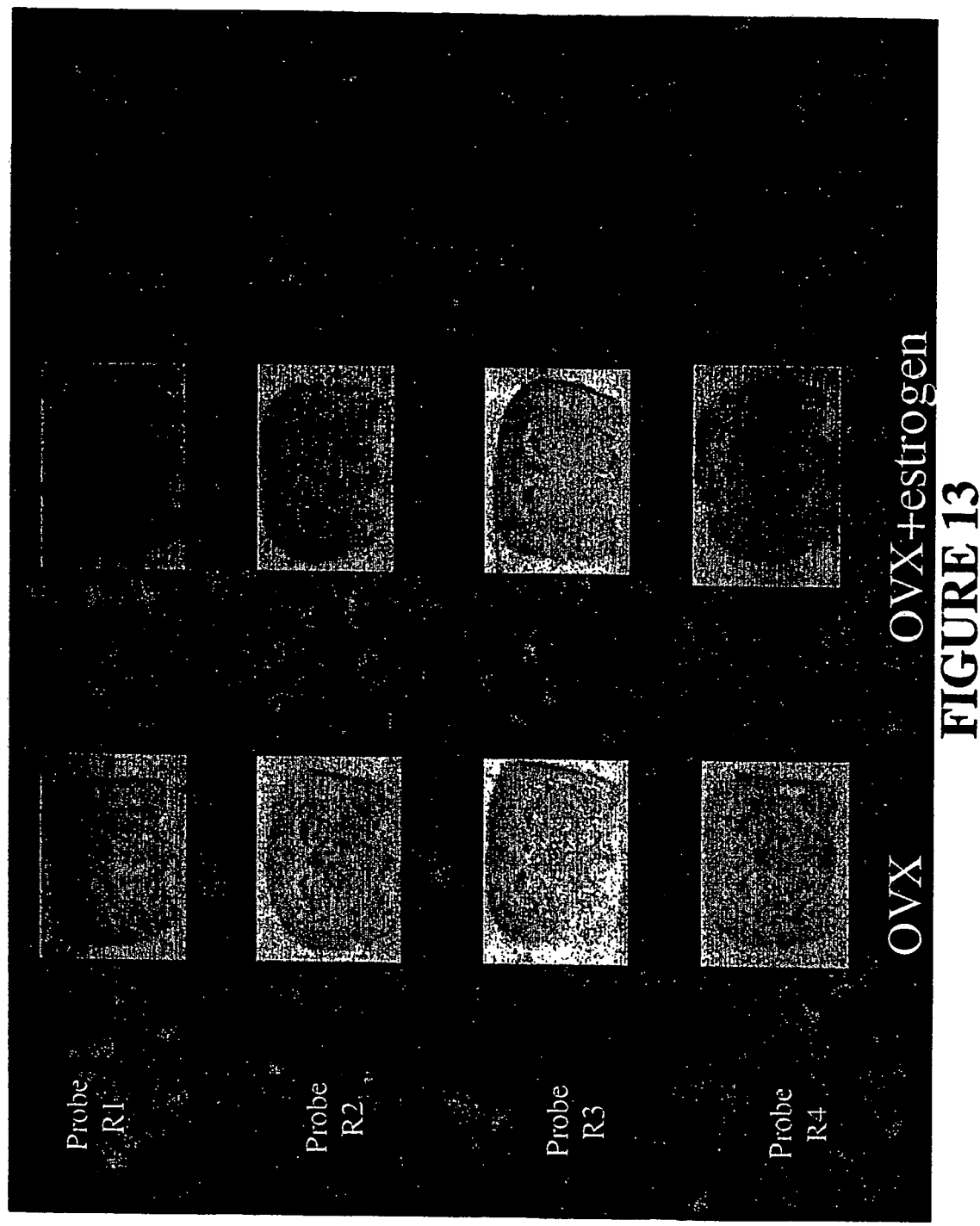
FIG. 13 shows increased hybridization of a DNA probe to neprilysin mRNA in rat brain of ovariectomized rats treated with estrogen. The left-most column of images show hybridization of probes R1 through R4 to rat brain from ovariectomized rats (control). The right-most column of brain sections shows hybridization of probes R1 through R4 to rat brain from ovariectomized rats treated with estrogen (right column). R1, R2, and R3 correspond to the type 1, type 2, and type 3 forms of neprilysin mRNA (see Li, C., Booze, R. M., and Hersh, L. B. *Tissue Specific Expression of Rat Neutral Endopeptidase (Neprilysin) mRNAs.* J. Biol. Chem. 270, 5723-5728 (1995) and Booze R M, Li C, Hersh L. B. *Differential expression of neprilysin enkephalinase' mRNA transcripts in rat brain.* Neurosci. Res. Comm. 27, 45-55 (2000). R4 corresponds to total neprilysin mRNA.
Figure 14:
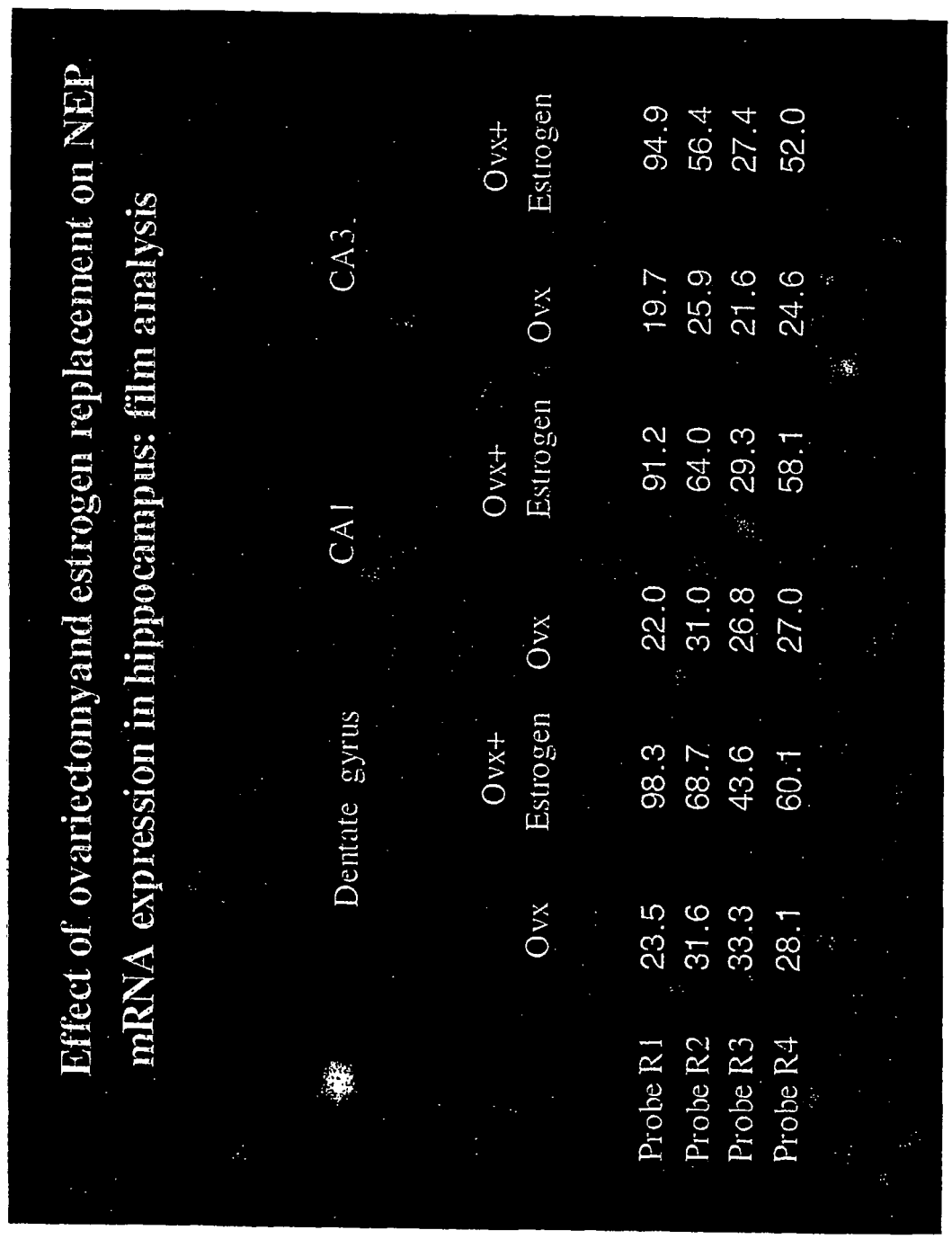
FIG. 14 shows the quantitative effect of ovariectomy and estrogen replacement on neprilysin mRNA expression in rat hippocampus based on film analysis of FIG. 13.

Referring to FIG. 13, the left hand column of images represents the control, in situ hybridization of each of the probes R1 through R4 in brain sections from ovariectomized rats without estrogen treatment. The right hand column of images represents the in situ hybridization for each of the probes R1 through R4 with the test group, brain sections from ovariectomized rats that received estrogen treatment. The dark and shaded areas represents hybridization by the probes in each of the samples. The antisense R1 probe in brain cells of ovariectomized rats that were treated with estrogen exhibited the highest degree of hybridization in the rat brain FIG. 14 quantifies the results of FIG. 13 in various regions of the hippocampus including the dentate gyrus and CA 1 and CA 3 regions. Accordingly, the expression of neprilysin mRNA in the hippocampus is about 300% higher in the group of ovariectomized rats treated with estrogen then in the group of rats that were ovariectomized, but did not received estrogen.

Example 16

Neprilysin Enzyme Activity

The tissue lysates were evaluated for neprilysin enzymatic activity using a two-step chromogenic assay. In the first reaction glutaryl-Ala-Ala-Phe-4-methoxy-2-naphthylamide is cleaved by neprilysin to Phe-4-methoxy-2-naphthylamide, while in the second step an aminopeptidase is used to generate the fluorescent 4-methoxy-2-naphthylamine. Reaction mixtures in 100 μL volumes containing 100 μM glutaryl-Ala-Ala-Phe-4 methoxynaphthylamide, 50-100 μg membrane fraction, and 20 mM MBS buffer were added to a 96 well microtiterplate. Incubations were for 2 hours at 37° C. in a water bath. At the end of the incubation period, the reaction was terminated by the addition of phosphoramidon. Leucine aminopeptidase was added and the mixtures were incubated for an additional 15 minutes. The 4-methoxy-2-naphthylamine was quantified spectrofluorimetrically at an excitation wavelength of 340 nM and an emission wavelength of 425 nM. Free 4-methoxynaphthylamine was used to construct a standard curve.

The enzyme preparation from each tissue was assayed five times. In addition, triplicate incubations with each tissue preparation were conducted in parallel in the presence of phorphoramidon (50 µM, a specific inhibitor of neprilysin. Protein in the tissue preparations was quantified by the bicinchoninic acid method using BCA Protein Assay Reagent Kit (Pierce).

Referring to FIG. 15, the effects of ovariectomy and estrogen replacement on neprilysin activity in rat brain are set forth. There was approximately a 30% increase in neprilysin activity in the hippocampus of ovariectomized and estrogen treated rats over ovariectomized rats that were not treated with estrogen.

Example 17

A Peptide Increases Insulysin Enzyme Activity

Figure 16:
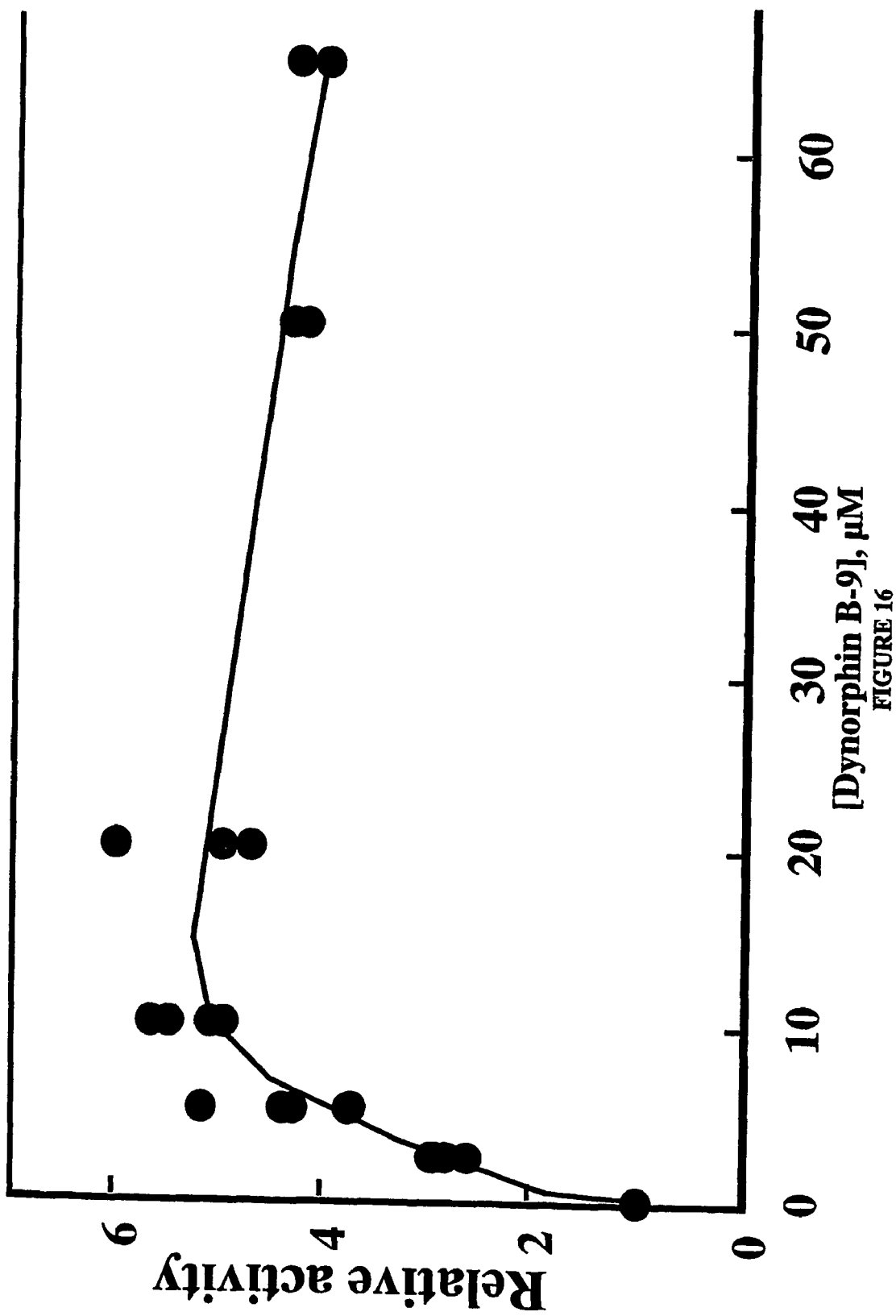
FIG. 16 shows the effect of a peptide, dynorphin B-9, on increasing the activity of purified insulin degrading activity.

Referring to FIG. 16, the effect of increasing the concentration of the peptide dynorphin B-9 on insulysin activity is shown. Insulysin activity was measured with the fluorogenic peptide Abz-GGFLRKHGQ-EDDnp (SEQ ID No: 14) in the presence of increasing concentrations of the peptide. This peptide contains the fluorescent 2-aminobenzyl (Abz) which is internally quenched by the 2,4-dinitrophenyl moiety. Cleavage at a peptide bond leads to an increase in relief of quenching and an increase in fluorescence (Csuhai, E., Juliano, M. A., Pyrek, J. S., Harms, A. C., Juliano, L. and Hersh, L. B. *New Fluorogenic Substrates for N-Arginine Dibasic Convertase*. Anal. Biochem. 269, 149-154, (1999). The curve shows an enhancement of insulysin activity. As a control trypsin hydrolysis of the same peptide showed inhibition, not activation, by dynorphin B-9.

Example 18

A Number of Peptides Increases Insulysin Enzyme Activity

Referring to FIG. 17, the effect of increasing the concentration of several different peptides on insulysin activity is summarized. Insulysin activity was measured with the fluorogenic peptide Abz-GGFLRKHGQ-EDDnp (SEQ ID NO: 14) in the presence of increasing concentrations of the peptide. This demonstrates the generality of the activation process.

All of the references cited herein are incorporated by reference in their entirety.

Those skilled in the art will recognize, or be able to ascertain using no more than routine experimentation, many equivalents to the specific embodiments of the invention specifically described herein Such equivalents are intended to be encompassed in the scope of the following claims.

What is claimed is:

1. An in vitro method of identifying a candidate compound for use in reducing formation or growth of amyloid plaque or for reducing amyloid peptide neurotoxicity, comprising:
    (a) assessing the effect of a test compound on activity of an insulin degrading enzyme (IDE), wherein activity is measured as effect of the test compound on the affinity of the IDE for an IDE substrate or the test compound, rate of IDE substrate cleavage, or stability of the IDE, relative to a control lacking the test compound, wherein the test compound is selected from the group consisting of:
    a peptidomimetic, analog of a peptide activators, peptide derivative or analog of Aβ, saccharide, fatty acid, purine, pyrimidine, nucleic acid, derivative or analog thereof, complex organic or simple or complex inorganic molecules, metal-containing compounds, steroids, or steroid analog, fluorogenic peptide, or derivative or analog thereof and any such molecules in combination; and
    (b) identifying the test compound as a candidate compound for use in reducing formation or growth of amyloid plaque or for reducing amyloid peptide neurotoxicity if it enhances the activity or stability of said IDE.

2. The method of claim 1, wherein said test compound is fluorogenic peptide Abz-GGFLRKHGQ-EDDnp (SEQ ID NO: 14) thereof.

3. The method of claim 1 wherein activity is assessed by measuring the effect of the test compound on the affinity of the IDE for an IDE substrate.

4. The method of claim 3 wherein the substrate is labeled with a detectable label.

5. The method of claim 3 wherein the substrate is monitored via high performance liquid chromatography.

6. A method of
    assessing the effect of a test compound on insulysin activity and ability to degrade Aβ, comprising contacting said test compound with an extract comprising insulysin and identifying a test compound that enhances insulysin activity or stability wherein insulysin activity is measured as effect of the test compound on the affinity of insulysin for a substrate or the test compound, rate of insulysin substrate cleavage, or stability of the insulysin, relative to a control lacking the test compound, wherein the test compound is selected from the group consisting of:
    a peptidomimetic, analog of a peptide activator, peptide derivative or analog of Aβ, saccharide, fatty acid, purine, pyrimidine, nucleic acid, derivative or analog thereof, complex organic or simple or complex inorganic molecules, metal-containing compounds, steroids, or steroid analog, fluorogenic peptide, or derivative or analog thereof and any such molecules in combination.

7. The method of claim 6, wherein said test compound is peptide Abz-GGFLRKHGQ-EDDnp (SEQ ID NO: 14).

* * * * *